United States Patent [19]

McEwan

[11] Patent Number: 5,573,012
[45] Date of Patent: Nov. 12, 1996

[54] BODY MONITORING AND IMAGING APPARATUS AND METHOD

[75] Inventor: Thomas E. McEwan, Livermore, Calif.

[73] Assignee: The Regents of the University of California, Oakland, Calif.

[21] Appl. No.: 287,746

[22] Filed: Aug. 9, 1994

[51] Int. Cl.⁶ ..................................................... A61B 5/11
[52] U.S. Cl. ....................... 128/782; 128/653.1; 128/721
[58] Field of Search ................................... 128/782, 774, 128/721, 653.1, 782, 721, 774, 653.1

[56] References Cited

U.S. PATENT DOCUMENTS

| | | | |
|---|---|---|---|
| 3,334,622 | 8/1967 | Brech | 128/653.1 |
| 3,875,929 | 4/1975 | Grant | 128/653.1 |
| 4,248,244 | 2/1981 | Charnitski et al. | 128/706 |
| 4,743,906 | 5/1988 | Fullerton | 342/27 |
| 4,907,596 | 3/1990 | Schmid et al. | 128/672 |
| 4,979,186 | 12/1990 | Fullerton | 375/23 |
| 4,991,585 | 2/1991 | Mawhinney | 128/653.1 |
| 5,030,956 | 7/1991 | Murphy | 342/22 |
| 5,220,922 | 6/1993 | Barany | 128/721 |
| 5,227,797 | 7/1993 | Murphy | 128/653.1 |
| 5,272,513 | 12/1993 | Vahala et al. | 356/28 |
| 5,321,501 | 6/1994 | Swanson et al. | 356/345 |
| 5,363,108 | 11/1994 | Fullerton | 342/27 |
| 5,391,199 | 2/1995 | Ben-Haim | 607/122 |

Primary Examiner—William E. Kamm
Assistant Examiner—Carl H. Layno
Attorney, Agent, or Firm—Henry P. Sartorio

[57] ABSTRACT

A non-acoustic pulse-echo radar monitor is employed in the repetitive mode, whereby a large number of reflected pulses are averaged to produce a voltage that modulates an audio oscillator to produce a tone that corresponds to the heart motion. The antenna used in this monitor generally comprises two flat copper foils, thus permitting the antenna to be housed in a substantially flat housing. The monitor converts the detected voltage to an audible signal with both amplitude modulation and Doppler effect. It further uses a dual time constant to reduce the effect of gross sensor-to-surface movement. The monitor detects the movement of one or more internal body parts, such as the heart, lungs, arteries, and vocal chords, and includes a pulse generator for simultaneously inputting a sequence of pulses to a transmit path and a gating path. The pulses transmitted along the transmit path drive an impulse generator and provide corresponding transmit pulses that are applied to a transmit antenna. The gating path includes a range delay generator which generates timed gating pulses. The timed gating pulses cause the receive path to selectively conduct pulses reflected from the body parts and received by a receive antenna. The monitor output potential can be separated into a cardiac output indicative of the physical movement of the heart, and a pulmonary output indicative of the physical movement of the lung.

23 Claims, 12 Drawing Sheets

BODY MONITORING AND IMAGING APPARATUS AND METHOD

STATEMENT OF GOVERNMENT RIGHTS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates in general to the medical field, and more particularly to monitors and methods for detecting, monitoring and measuring the movement of the heart, lungs and other body organs, tissues and members, and for processing corresponding bio-potential signals.

1. Stethoscopes and Acoustic Monitors

In the field of cardio-pulmonary monitoring, it has been the general practice to employ microphonic, voltaic, pressure or strain gauge devices to pick up the beats of the cardio-vascular organs of a living person or animal. One such device is the acoustic stethoscope invented in the early nineteenth century by Theophile-Rene Laennec to diagnose chest disease in living patients, by studying the character of the sounds produced by damaged tissues. The Laennec stethoscope represented a substantial improvement over the hollow reed in use at that time. It is presently very commonly used, and has remained almost unchanged over the last century.

Continuous developments are being attempted to make use of the advanced state of the art technology, in order to enhance conventional cardiopulmonary monitors. Examples of existing cardiopulmonary monitors and of the trend of their development are illustrated in the following patents, all of which are incorporated herein by reference:

| U.S. Pat. No. | Patentee | Issue Date |
| --- | --- | --- |
| U.S. 4,903,794 | Klippert et al. | 02-27-1990 |
| U.S. 4,972,841 | Iguchi | 11-27-1990 |
| U.S. 4,991,581 | Andries | 02-12-1991 |
| U.S. 4,997,055 | Grady | 03-05-1991 |
| U.S. 5,003,605 | Phillipps et al. | 03-26-1991 |
| U.S. 5,010,889 | Bredesen et al. | 04-30-1991 |
| U.S. 5,010,890 | Pfohl et al. | 04-30-1991 |
| U.S. 5,012,820 | Meyer | 05-07-1991 |
| U.S. 5,022,405 | Hok et al. | 06-11-1991 |
| U.S. 5,025,809 | Johnson et al. | 06-25-1991 |
| U.S. 5,027,825 | Phelps et al. | 07-02-1991 |
| U.S. 5,213,108 | Bredesen et al. | 05-25-1993 |
| U.S. 5,218,969 | Bredesen et al. | 06-15-1993 |
| U.S. 5,288,954 | Peart | 02-22-1994 |
| U.S. 5,295,489 | Bell et al. | 03-22-1994 |

Most of these devices operate on acoustic principles, and basically amplify sounds generated by the heart and lungs. The Klippert et al. U.S. Pat. No. 4,903,794 describes a stethoscope for auscultating sounds from a subject, which includes a curvilinear convex diaphragm and an acoustic chamber communicating with the diaphragm for enhancing the fidelity of the received sounds.

The Iguchi U.S. Pat. No. 4,972,841 describes a miniaturized electronic stethoscope designed to be used in conjunction with a standard sphygmomanometer in the measurement of blood pressure and pulse rate simultaneously in which a transducer converts the Korotkoff sounds into electrical signals. These electrical signals are amplified and fed to a counter in which the detected pulse rate per unit time is calculated and then the result is displayed as a digital pulse rate.

The Andries U.S. Pat. No. 4,991,581 discloses an acoustic apparatus for processing acoustics, such as body sounds, for assessment of the sound and possible diagnosis of abnormalities associated with the sound. The Grady U.S. Pat. No. 4,997,055 illustrates a multiple channel stethoscope which provides the user with continuous access to physiological sounds. The stethoscope may enhance sound conduction by producing constructive interference of sound waves.

The Phillipps U.S. Pat. No. 5,003,605 shows an electronically augmented stethoscope with timing sound, which simultaneously provides the listener combined unmodified, familiar audible sounds and sounds which have been electronically augmented to bring them within the human auditory range. The Bredesen U.S. Pat. Nos. 5,010,889 and 5,218,969 describe a stethoscope which performs auscultation, and which is supposed to automatically diagnose abnormalities based on body sounds. The body sounds are recorded from a plurality of locations on the body, digitized, stored in memory, and categorized according to specific characteristics.

The Pfohl U.S. Pat. No. 5,010,890 describes a vital sign monitoring system for monitoring the vital signs of a patient, particularly prior to and during anesthesiology, during and after operational procedures. This monitoring system includes a sensor unit having a microphone for mounting on the patient's chest for picking up breath and heart sounds, and can be used with an esophageal stethoscope.

The Meyer U.S. Pat. No. 5,012,820 illustrates a device for investigation of muscular contraction, by determining the change in the mechanical magnitudes during muscular contraction, and for correlating this change to the change in the electrical magnitudes of nerve and muscle during muscular contraction. Electrodes are arranged above the contracting muscle or its nerve and/or a stethoscope head, with a microphone arranged above the muscle.

The Hok et al. U.S. Pat. No. 5,022,405 discloses a stethoscope for use with nuclear magnetic resonance (NMR) screenings in order to supervise a bell chest piece adapted to pick up audible heart and breathing sounds or other bodily sounds from the patient. The stethoscope includes a microphone member adapted to be arranged at the opposite side of a tube outside the zone of the maximum field strength of the NMR equipment and adapted to convert the acoustic signals into corresponding signals. The Johnson et al. U.S. Pat. No. 5,025,809 relates to a method for identifying characteristic phonocardiographic heart sounds using a recording digital stethoscope.

The Phelps et al. U.S. Pat. No. 5,027,825 describes a self-contained stethoscope transmitter having a pickup head housing which defines a precordial dome for contact with a patient whose bodily sounds are to be observed and/or monitored, and electronic circuitry positioned within the housing for receiving the sounds, converting them into FM signals, and transmitting these FM signals. The Bredesen et al. U.S. Pat. No. 5,213,108 illustrates a visual display stethoscope for use in the auscultation of body sounds. The stethoscope is adapted for display, manipulation and analysis of the received body sounds.

The Peart et al. U.S. Pat. No. 5,288,954 illustrates a connector for joining one end of a rigid stethoscope ear tube to a multiple leaf spring within a flexible tube that is attached to the stethoscope chestpiece. The Bell et al. U.S. Pat. No.

5,295,489 describes an endotracheal tube, stethoscope and thermistor combination for allowing simultaneous patient ventilation, vital sounds monitoring, and body core temperature monitoring by a single instrument.

These monitoring devices suffer from serious drawbacks, among which are the following: The acoustic spectrum of these devices is low, and lies within the lower end of the auditory spectrum, i.e., 100 Hz or below, thus rendering the body sounds difficult to hear. Although the body organs and parts exhibit substantial motion, they are inherently quiet, and the sounds generated thereby are quite low and faint and do not provide a significant acoustic signature. Conventional stethoscopes and electronic stethoscopes with microphones that produce amplified sounds in an earpiece, headphone or on a visual display, and which rely on finger and surface contact to the microphone or bell/diaphragm, produce microphonic effects (i.e., noise) which could be louder than the body sounds to be detected, thus forcing the patients and the attending medical staff to hold very still in a quiet room.

Additionally, the body sounds are not detectable through clothing, and the patients must inconveniently undress in order to effectively use these conventional stethoscopes. Another factor which further compounds the foregoing drawbacks is that stethoscopes are used by non-professional users for home health care. Most of the likely users of the acoustic devices tend to be elderly with heart disease, and are hard of hearing. Yet another drawback of the conventional low cost devices relates to their use for health maintenance, such as in athletics and sporting events, which require continuous monitoring of the heart rate, and close contact with the body. One such device is the blood pressure monitor watch sold by Casio Company. Pressure sensing monitors and electrical pulse sensors must maintain tight mechanical or electrical skin contact to function, and are therefore prone to intermittent operation during intense physical activity.

The Chartinitski et al. U.S. Pat. No. 4,248,244, which is also incorporated by reference, discloses a method and an indicator for measuring heart beat rate having electrodes for coupling to the electrical impulses corresponding to each beat of the heart. These electrodes are connected to an electronic circuit for producing a burst of alternating electronic signals in response to the each electrical impulse produced at each heart beat.

Therefore, there is an evident and still unsatisfied need for a new non-invasive, non-acoustic monitor and method for monitoring the wall movement of the heart, lungs and other body organs, tissues or members, and for processing corresponding bio-potential signals. The new monitor should significantly reduce if not completely eliminate microphonic effects, and should be capable of detecting intra-body movement through clothing, or at some distance, without requiring the patients to undress. The new monitor should be relatively inexpensive, and simple to use by non-professional users for home health care and in athletics and sporting events. The monitor should be adapted to replace or to be used in conjunction with existing devices to perform various functions and to be used in a multitude of corresponding applications, including, but not limited to those exemplified by the above listed patents.

2. Ultrasound Monitors and Magnetic Resonance

Ultrasound monitors have been developed to detect the position and movement of body organs. These monitors have also been used with other imaging devices, such as nuclear magnetic imaging (NMI)/nuclear magnetic resonance (NMR) systems. Examples of existing ultrasound monitors and magnetic resonance imaging systems are illustrated in the following patents, all of which are incorporated herein by reference:

| U.S. Pat. No. | Patentee | Issue Date |
|---|---|---|
| U.S. 5,000,182 | Hinks | 03-19-1991 |
| U.S. 5,032,793 | Yamamoto et al. | 07-16-1991 |
| U.S. 5,062,427 | Seo et al. | 11-05-1991 |
| U.S. 5,099,847 | Powers et al. | 03-31-1992 |
| U.S. 5,152,290 | Freeland | 10-06-1992 |
| U.S. 5,295,485 | Shinomura et al. | 03-22-1994 |

The Hinks U.S. Pat. No. 5,000,182 describes a cardiac synchronization magnetic resonance imaging device for monitoring the cardiac cycles of a patient in an examination region. An imaging sequence trigger enables an image sequence controller to start an imaging sequence in an imaging window in conjunction with the R-wave. The imaging sequence starts immediately with the R-wave such that the end-diastole stage of the heart is imaged.

The Yamamoto et al. U.S. Pat. No. 5,032,793 discloses an NMR gated imaging apparatus in which an ultrasonic pulse signal is repeatedly transmitted toward the heart of a human body from an ultrasonic transducer to detect the position of the heart on the basis of the time of detection of a peak of an echo signal. The excitation and measurement of an NMR signal is executed only when a peak detector generates a detection output signal having a level included in a predetermined range.

The Seo et al. U.S. Pat. No. 5,062,427 illustrates an ultrasonic Doppler apparatus which includes an input device connected to a blood flow imaging device which is a color Doppler tomograph constituted by combining a sector electronic scanning type ultrasonic diagnostic device and a Doppler system to derive blood flow information and tomographic image information by using a single ultrasonic probe.

The Powers et al. U.S. Pat. No. 5,099,847 teaches a technique for increasing the display frame rate of a medical ultrasound system. The system receives trigger signals based upon the occurrence of a predetermined event in a subject's cardiac cycle, such as an R-wave. In response to these trigger signals, the ultrasound system acquires a series of frames representing a portion of the subject's body at an associated acquisition time.

The Freeland U.S. Pat. No. 5,152,290 relates to a method for recording ultrasound images to diagnose heart and coronary artery disease. Heart performance is evaluated by collecting ultrasound images of at least one chamber of the heart of a patient after peak exercise. The images are subsequently displayed and analyzed to determine the presence and degrees of heart disease. Collecting the images is done continuously at a rate of at least eight images per heart beat.

The Shinomura et al. U.S. Pat. No. 5,295,485 describes an ultrasonic diagnostic system which includes a probe composed of a group of transducers for transmitting and receiving an ultrasonic wave to display a sectional image of a patient's body. In some applications, this system is supposed to replace the stethoscope.

These conventional monitors are generally bulky, relatively expensive to acquire, operate and maintain, technically complex and cannot be operated by non-professional technicians. Additionally, the ultrasound waves do not propagate well through bone, such as the ribs or sternum, or thick fat layers, and further they do not propagate well through air, and could require index matching lubricant between the sensor and the chest wall. Also, these monitors suffer from some of the foregoing drawbacks associated with acoustic stethoscopes.

Therefore, there is a great need for a new non-invasive, non-ultrasonic monitor and method for monitoring the wall movement of the heart, lungs and other body organs, tissues and members, and for processing corresponding bio-potential signals. The new monitor should significantly reduce if not completely eliminate microphonic effects, and should be capable of detecting intra-body movement through clothing. The new monitor should be relatively inexpensive, and simple to use by non-professional users. It should be adapted to replace or to be used in conjunction with existing devices to perform various functions and to be used in a multitude of corresponding applications, including, but not limited to those exemplified by the above listed patents.

3. Optical Imaging Technology

Another technique for monitoring moving objects such as the heart, is described in the Slump et al. U.S. Pat. No. 5,040,201, which is incorporated herein by reference. This patent discloses an X-ray exposure synchronization method for imaging the heart in response to periodic pulses generated at instances in the period at which the hazard is anticipated to be in a given position. The limitations of this technology should be readily apparent to those skilled in the art. Additionally, this technology is not readily available to non-professional users for everyday use.

Yet another optical imaging method is described in U.S. Pat. No. 5,321,501 to Swanson et al., which is incorporated herein by reference. This patent generally relates to the optical imaging of a sample wherein longitudinal scanning is provided by either varying relative optical path lengths for an optical path leading to the sample and to a reference reflector, or by varying an optical characteristic of the output from an optical source. A transverse scanning is also disclosed.

Therefore, there is still a need for a new imaging and monitoring device which can replace, or be used in conjunction with existing X-ray technology and other imaging techniques, for monitoring the movement of intra-body organs, tissues, and other structures and foreign objects embedded in a human or animal body.

SUMMARY OF THE INVENTION

Accordingly, it is an object of the present invention to provide a sensing device which addresses the problems presented by the conventional monitoring devices, and which provides adequate solutions thereto.

It is another object of the present invention to provide a non-invasive, non-acoustic monitor and method for monitoring the wall or tissue movement of the heart, lungs and other body organs and members, rather than the acoustic signature associated with that movement, and for processing corresponding bio-potential signals.

It is yet another object of the present invention to provide a new non-acoustic monitor which significantly reduces if not completely eliminates microphonic effects.

It is still another object of the present invention to provide a new non-acoustic monitor which is capable of detecting intra-body movement through the user's clothing, or at some distance from the body.

It is a further object of the present invention to provide a new non-acoustic monitor which is relatively inexpensive, and simple to use by non-professional users for home health care, patient monitoring, and in athletics and sporting events.

It is another object of the present invention to provide a new non-acoustic monitor which is adapted to replace, or to be used in conjunction with existing devices, to perform various functions and to be used in a multitude of corresponding applications.

It is yet another object of the present invention to provide a new non-acoustic monitor which generates a strong output centered in the audible spectrum.

It is still another object of the present invention to provide a new non-acoustic monitor which generates both amplitude and velocity information.

It is a further object of the present invention to provide a new non-acoustic monitor which provides depth information about the organ, tissue or structure being scanned.

It is an additional object of the present invention to provide a new non-acoustic monitor which generates an audible stereo image of the walls of an organ.

It is another object of the present invention to provide a new non-invasive, non-ultrasonic monitor and method for monitoring the wall or tissue movement of the heart, lungs and other body organs and members, and for processing corresponding bio-potential signals.

It is also an object of the present invention to provide a new imaging and monitoring device and method, which can replace existing X-ray technology, for use to monitor the movement of intra-body organs, tissues, and other structures and foreign objects embedded in a human or animal body.

It is a further object of the present invention to provide a new cardiac and pulmonary monitor which eliminates electrodes and concomitant skin conditions.

Briefly, the above and further objects and advantages of the present invention are realized by a new monitor for detecting heart motion based on the emission and detection of very short voltage pulses. A pulse-echo radar mode is employed in the repetitive mode, whereby a large number of reflected pulses are averaged to produce a voltage that modulates an audio oscillator to produce a tone that corresponds to the heart motion. The antenna used in this monitor generally comprises two flat copper foils, thus permitting the antenna to be housed in a substantially flat housing. The monitor converts the detected voltage to an audible signal with both amplitude modulation and Doppler effect. It further uses a dual time constant to reduce the effect of gross sensor-to-surface movement.

Another embodiment of the present invention includes an apparatus for detecting and monitoring cardiac and respiratory motion through materials such as mattress pads. Non-contact operating range can be greater than 12 inches. The apparatus is also based on the emission and detection of very short voltage pulses in a pulse-echo radar mode. A large number of reflected pulses are averaged to produce a voltage that is modulated by reflections from the heart, arteries and lungs.

Due to the relative simplicity of the inventive design, the monitors according to the present invention can be produced very inexpensively. Furthermore, the circuitry can be integrated onto a single low cost silicon chip based on a 2 micron CMOS process. The antennas in the heart and respiratory monitor are formed of simple wires that may be embedded in a mat, mattress or seat back along with the circuitry to provide a low cost life monitor, i.e., to determine whether the person lying on the mat or sitting on the chair is still alive, or when that person's life signs have changed.

One potential application for the foregoing feature is to distinguish the presence of living persons or animals from inanimate objects in any environment, such as people buried under rubble or not readily visible. In such applications, gross motion may be sensed, or preferably, respiration can be sensed. Respiration monitoring provides for a good discrimination between living persons (or animals) and inanimate objects, even if the latter objects are jiggling, since jiggling typically occurs on a time scale of 2 seconds or less (greater than 0.5 Hz), whereas respiration typically occurs on a time scale of longer than 2 seconds (less than 0.5 Hz). Accordingly, with dual band filters, the monitor according to the present invention can discriminate between the jiggling motion of inanimate objects and the breathing and jiggling motion of living beings. This level of discrimination can control and/or be associated with the deployment of various mechanisms. Enhancements for the present monitors are also foreseeable, such as by adding a high power transmitter/step generator and a reflector antenna for improved range/sensitivity. These monitors would thus be useful for disaster victim detection.

The present monitor non-acoustically detects the mechanical movement of one or more internal body pads, such as the heart, lungs, arteries, veins, fetus heart beats, vocal chords, etc., and includes a pulse generator for simultaneously inputting a sequence of pulses to a transmit path and a gating path. The pulses transmitted along the transmit path drive an impulse generator and provide corresponding transmit pulses that are applied to a transmit antenna.

The gating path includes a range delay generator which generates timed gating pulses. The timed gating pulses cause the receive path to selectively conduct pulses reflected from the body parts and received by a receive antenna. The monitor output potential can be separated into a cardiac output indicative of the physical movement of the heart, and a pulmonary output indicative of the physical movement of the lung.

The timed gating pulses of the monitor gate a sample and hold circuit along the receive path. The monitor further includes a dual time constant circuit whereby, for large signals related to gross sensor motion relative to pulmonary motion, there is a fast AC coupling time constant, and for normal signal levels related to heart motion there is a much slower AC coupling time constant.

BRIEF DESCRIPTION OF THE DRAWINGS

The above and other features of the present invention and the manner of attaining them, will become apparent, and the invention itself will be best understood, by reference to the following description and the accompanying drawings, wherein.

DETAILED DESCRIPTION OF THE PREFERRED EMBODIMENTS

Figure 1:
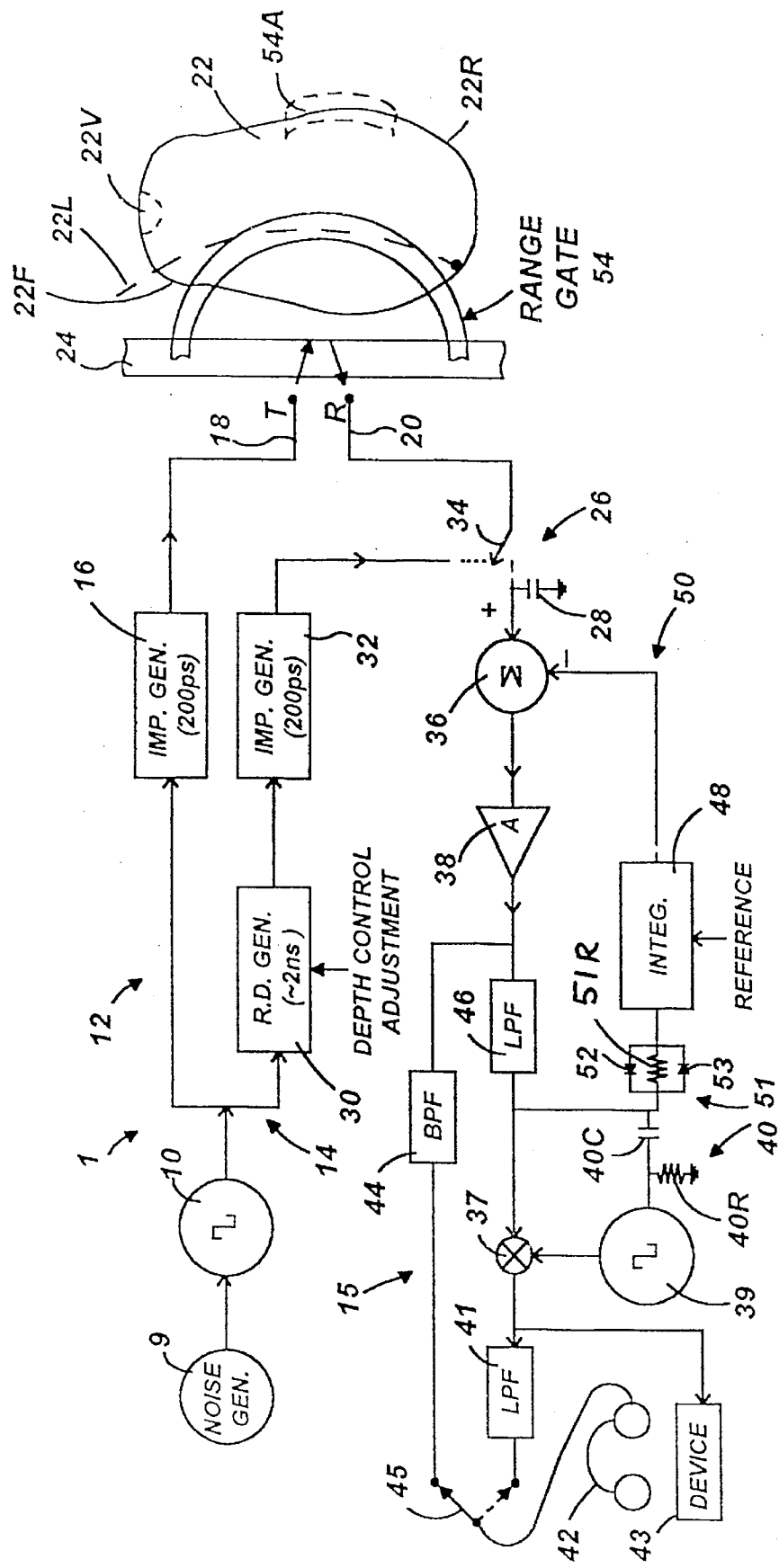
FIG. 1 is a block diagram of a new cardiac monitor according to the present invention.

The general operation of the inventive monitor is based on the emission of a pulse from a transmit antenna, waiting for a brief period of time, and then opening a gate connected to a receive antenna to allow the reflected pulse to be sampled. In one application, where the monitor is used as a stethoscope, the waiting period corresponds to about one inch of round trip time of flight at the speed of light in tissue. In another exemplary application, where the inventive monitor is used as a non-contact cardiopulmonary monitor, the waiting period corresponds to 12 inches or more of round trip time of flight at the speed of light in free space (or in a combination of free space and one inch of tissue). It has been experimentally determined that respiration can be detected at a distance of 11 feet.

The above process is repeated at 1 MHz, rate, allowing approximately 10,000 receive pulses to be averaged prior to driving ancillary equipment, including but not limited to audible or visual displays. In essence, the bio-potential signals output by the inventive monitor can be processed as needed.

The high level of averaging reduces the random noise accompanying the sampled signal to such an extent that extremely low amplitude signals can be detected. Repetitive operation also leads to extreme simplification of the entire circuit.

The averaged pulses provide a voltage level that corresponds to the radar reflectivity at a range defined by the delay between the emitted pulse and the time of gating, or operating a sampler circuit cooperating with the receive antenna. This process is referred to as "range gating", and provides depth information about the organ, tissue, membrane or other structure being scanned.

The inventive monitor is capable of sweeping, scanning or imaging the "range gate" (i.e., the region being scanned), and it senses reflectivity at a predetermined depth. As the heart muscle moves through the range gate, it changes the reflectivity within the range gate. A motion sensor based on these principles is described in copending U.S. patent application Ser. No. 08/044,717, filed on Apr. 12, 1993, now U.S. Pat. No. 5,361,070 by Thomas E. McEwan, entitled "Ultra-Wideband Radar Motion Sensor", which is incorporated herein by reference. The gate is typically held open only for a duration equal to the emitted pulse width. The present invention also utilizes an ultra-wideband receiver described in copending U.S. patent application Ser. No. 08/044,745 filed Apr. 12, 1993 by Thomas E. McEwan, entitled "Ultra-Wideband Received", which is incorporated herein by reference.

Accordingly, the invention is based on the pulse-echo radar principle of clocking the two-way time of flight of an electromagnetic pulse. As used herein, the term radar impulse refers to a short radiated pulse, which replaces the long sinusoidal burst used in conventional radar technology. There is no specific frequency associated with impulse radar; rather, its frequency spectrum is related by the Fourier transform of the impulse.

The free-space radiated impulse is a half-sine pulse about 200 ps wide. The antenna is typically shorter than one half wavelength of the highest frequency component in the voltage pulse. One of the important advantages of impulse radar is that the spectrum is located as low as possible, where tissue attenuation is the lowest. Other advantages include simplicity and low cost.

FIG. 1 thereof, illustrates a block diagram of a monitor 1. In this particular application, the monitor 1 is used as a stethoscope. However, it should be clear that the monitor 1 can be used in a variety of other applications.

A noise generator 9 modulates the pulse repetition frequency/pulse repetition interval (PRF/PRI) generator 10 to create a PRF with a 1 MHz average and 1–10% random variation about 1 MHz, i.e., a 1–10% PRF dither. The dither spreads the emission spectrum from antenna T to reduce potential interference to other spectrum users, and the dither also randomizes the samples of extraneous interfering signals appearing at receive antenna R that are taken by the receive sampler 26. The received signals at antenna R are sampled and averaged, where the randomized samples average to zero, substantially eliminating interference from other sources such as RF transmitters. The desired echoes are unaffected by the dithering since they are received at a fixed time shortly after they are transmitted and are not affected by the exact time of occurrence of the next repetition interval. Dithering provides spectrum compatibility with conventional RF users and allows multiple impulse monitors to be used in close proximity. The chance of sampling the short pulses emitted by other impulse systems is both random and extremely low, and the probability of sequentially sampling enough pulses from another impulse system to build up a coherent, detectable signal is extremely low.

Pulses from a 1 MHz pulse repetition frequency/interval (PRF/PRI) generator 10 are input into two parallel paths, a transmit path 12 and a gating path 14. In the transmit path 12, the PRF/PRI generator 10 drives an impulse generator 16, which provides a 5 V transmit pulse with a 200 ps pulse width that is applied to the transmit antenna (T) 18.

The receive antenna (R) 20 picks up the pulse reflected from a sample being scanned, and applies it to a sample/hold (S/H) circuit 26 that is gated by a gating pulse from the gating path 14. The sample can be a body organ, including but not limited to a heart 22 behind a chest wall 24, a fetus, the ovaries, the vocal chords, a bone, a blood clot (hematoma), the brain, spinal chord, muscle, prostate, thyrohyoid membrane, etc. For simplicity of illustration the object will be exemplified by the heart 22. The gating pulse is delayed by approximately 2 ns from the time that the transmit antenna 18 radiates the pulse. Pulses from the PRF/PRI generator 10 which are input into the transmit path 12 are simultaneously input into the gating path 14 where they pass through a range delay generator 30 followed by a impulse generator 32, which produces a 200 ps gating pulse for controlling a gating switch 34.

The range of the delay generator 30 is adjustably regulated to control the depth sensitivity or range gate of the monitor 1. In the present example, the pulse is delayed by about 2 ns, so that the range of the monitor 1 is about 1 inch to 2 inches in tissue. The gating pulse closes the switch 34 so that reflected pulses from the range gate are input into the sample/hold circuit (S/H) 26 along a receive path 15.

In the preferred embodiment, the S/H circuit 26 includes a capacitor 28 connected to ground. Reflections, or lack thereof, occurring 1 to 2 inches from the antenna 20 are thereby sampled. The size of the capacitor 28 in the sample/hold 26 circuit is sufficiently large that each sample only partially charges it, and approximately 10,000 samples are required for the circuit to reach an equilibrium with the receive antenna signal. In one exemplary design, the capacitor 28 is on the order of 100 picofarads. The product of the impedance of the receive antenna 20 and the capacitance of capacitor 28 yields a time constant which is much greater than the width of the gate pulse, so it takes many pulses to charge capacitor 28.

Figure 2:
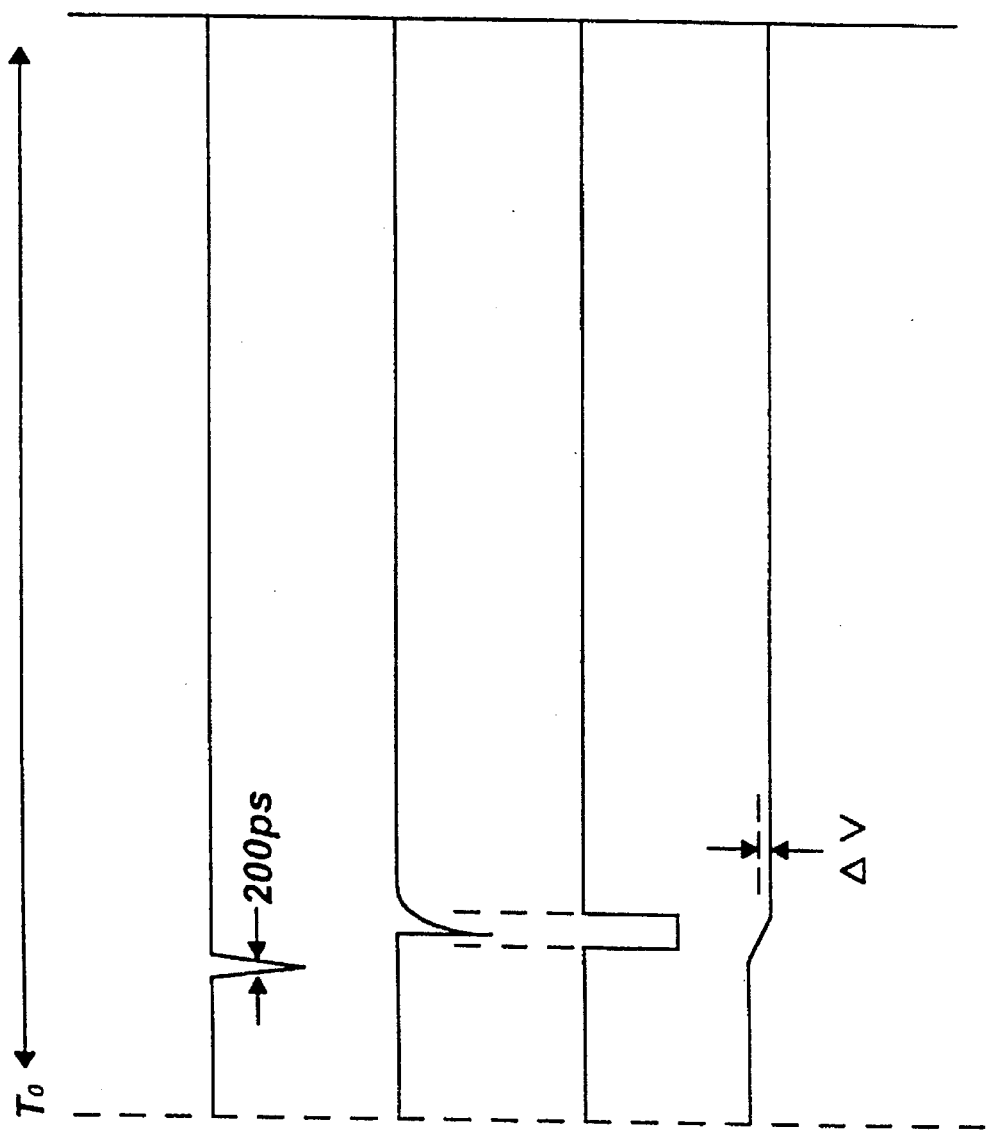
FIG. 2 is a timing diagram of the monitor of FIG. 1.

The timing relationship is shown in FIG. 2. The four waveforms are shown over a one pulse repetition interval (PRI). A 200 ps wide impulse is radiated from the transmit antenna 18. The reflected impulse from the receive antenna 20 coincides with the gating pulse. Each received pulse produces an incremental voltage change $\Delta V$ on the capacitor 28 of the S/H circuit 26. The capacitor voltage is the output of the averaging S/H circuit 26. The increment $\Delta V=1/N$ of the total received pulse, where N is the number of samples averaged, typically about 10,000. It should be understood that N can assume a different value.

The noise voltage at the sample/hold circuit 26 is reduced by a factor related to the square root of the number of samples averaged, 100 times in this case, and by a factor related to the effective time constant of the averaging circuit relative to the PRF of the system and the instantaneous bandwidth of the sampler—a factor stemming from the sampled data nature of the sample/hold circuit 26. In all, greater than 60 dB noise reduction is obtained compared to a circuit with 2 GHz bandwidth, i.e., the bandwidth of the radiated pulse.

The sample/hold output is applied to a voltage summation element or summer 36, which subtracts background reflections as described herein. The output of the summer 36 is amplified by an amplifier (A) 38, typically having 60 dB gain with a passband of DC to 16 Hz. A square wave generator or oscillator 39 has its output multiplied, by means of a multiplier 37, by the AC coupled amplitude of the voltage from the amplifier 38, and frequency modulated by the rate of change of the signal from the amplifier 38, thereby generating a Doppler effect that is related to the velocity of the heart muscle motion. The output of the amplifier 38 is fed to a band-pass filter 44 (20–5000 Hz), and therefrom to a selection switch 45 for allowing the audible detection of the sample movement such as the heart beat.

A low-pass filter 46 passes frequencies less than 20 Hz, and is connected to the output of the amplifier 38. The rate of change is derived from a differentiation circuit 40, which, in a simplified design, can be formed of an RC circuit comprising a capacitor 40C, typically on the order of 1 microfarad, and a shunt resistor 40R, typically on the order of 10 Kohms. A low pass filter 41 is used to attenuate the resulting harmonics at the output of the multiplier 37, in order to produce a pleasing audible tone via the earphone, loudspeaker or headphone 42.

While the bio-potential signals at the output of the amplifier 38, and the multiplier 37 are illustrated as input to the band-pass filter 44 and the low-pass filter 41 and headphone 42, respectively, it should be clear that these bio-potential signals can be alternatively, or simultaneously connected to a computer or other devices or systems 43, including, but not limited to a visual display, for providing visual indications and/or to drive, or work in conjunction with these devices or systems. If a visual display were used, such a display would include an arrangement of light emitting diodes (LED's) that sequentially light in proportion to the applied voltage, which is linearly related to the reflection magnitude of the pulse reflected from the heart 22.

The square wave generator 39 responds perceptibly at a level corresponding to approximately 1 microvolt appearing at the receive antenna 20. Since systematic errors in the sample/hold circuit 26, the summer 36, and the amplifier 38 may amount to several tens of millivolts, this error must be subtracted out in order to detect small changes, such as a 1 microvolt change caused by a small artery. In addition, surface reflections from the chest wall 24 contribute to the error voltage that must be subtracted.

For this purpose, an integrator 48 in the feedback path 50 of the amplifier 38 servo's the output of the amplifier 38 until an equilibrium is reached, such that the output of the amplifier 38 is forced to equal a reference voltage applied to the integrator 48. Since integrators have extremely high DC gain, the voltage difference between the output of the amplifier 38 and the reference voltage is reduced to a negligible value.

The integrator 48 in the feedback path 50 of the amplifier 38 is equivalent to a differentiator in its forward path, i.e., it makes the amplifier behave as if it were AC coupled. The advantage of using the integrator 48 is that it supplies the monitor bias current, subtracts errors in the amplifier 38, and permits the simple implementation of a dual time constant.

The overall response of the amplifier/integrator circuit is such that for large signals related to gross sensor motion relative to the patient's chest, there is a fast AC coupling time constant and for normal signal levels related to heart motion there is a much slower AC coupling time constant that allows for faithful reproduction of the heart motion. The dual time constant is provided by a dual time constant circuit 51, formed of two diodes 52, 53 shunted by a resistor 51R. Typically, the resistor 51R is on the order of 1 megaohm, and the diodes 52, 53 are common computer type diodes, such as 1N4148.

While not graphically illustrated, it should be understood that a suitable linear translation stage or other mechanism can be connected to the monitor 1 in order to move it either transversely or laterally relative to the sample (i.e., heart 22) to provide a two-dimensional or a multi-dimensional scanning. A similar mechanism may be provided to move the monitor 1 in the other transverse or lateral direction to provide multi-dimensional scanning of the sample.

Figure 3:
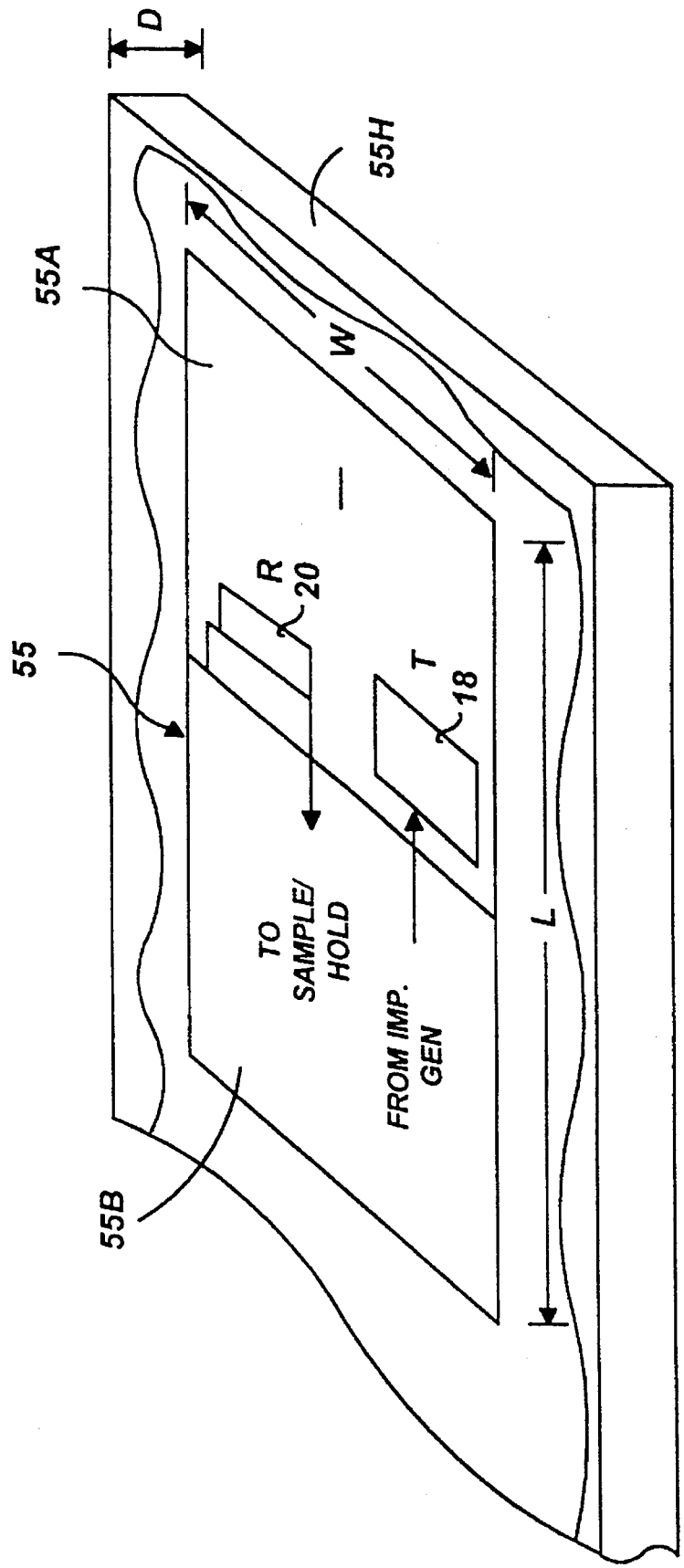
FIG. 3 is a schematic representation of an antenna forming part of the monitor of FIG. 1, and showing a cut-away view of a generally flat housing.

FIG. 3 depicts the geometry of the antennas 18, 20. As shown schematically in top view, the transmit antenna (T) 18 and the receive antenna (R) 20 are illustrated as generally rectangularly shaped patch antennas, made of copper foils, and having a side dimension ranging between ¼ to 1 inch. These antennas 18, 20 are formed on a dielectric holding substrate 55A of a circuit board 55, and are connected to a metal, such as copper, ground plane board 55B. In this particular example, the width W of the circuit board 55 is about 2 inches, and its length L is about 4 inches. The antennas 18, 20 are housed in a generally flat and thin housing 55H having a thickness D of about 0.75 inches.

An electromagnetic field is developed between the ground plane board 55B and the antennas 18, 20, to form a broadband monopole which couples well with a high dielectric constant material, such as the chest. The antennas 18, 20 are intended for close range monitoring, and are sized for the propagation of the waves within the body, which has a higher dielectric constant than air. As a result, in designing the range gate, or in "range gating" the monitor 1, the slower propagation velocity of the electromagnetic waves through the body tissues relative to air is taken into account. To this effect, the propagation impedance in free space $Z_0$(space) is:

$$Z_0(\text{space}) = \sqrt{\mu_0/\epsilon_0}\ ,$$

where $\mu_0$ is the permeability of vacuum and $\epsilon_0$ is the permittivity of vacuum. The propagation impedance in a material (such as muscle or body tissue) having $\epsilon_r=40$ is:

$$Z_0(\text{muscle}) = \sqrt{\mu_0/\epsilon_r\epsilon_0} = Z_0(\text{space})/\sqrt{\epsilon_r} = Z_0(\text{space})/\sqrt{40}\ .$$

Muscle propagation impedance is 60 ohms and the propagation impedance of blood ($\epsilon_r=60$) is 49 ohms. This difference in impedance causes a difference in the reflection magnitude between the heart muscle and its blood.

In a one dimensional analogy to propagation along a transmission line, which can be equated to time domain reflectometry (TDR), reflections off the heart muscle become equivalent to reflections from a transmission line discontinuity. The reflection coefficient, $\Gamma$, defined as $(Y-1)/(Y+1)$ where $Y=Z(\text{heart})/Z(\text{blood})$, can be applied to determine what fraction of the radiated pulse is returned. For example, the heart muscle with an $\epsilon_r=40$, has a reflection magnitude of 9.9% relative to blood. Thus, the difference in reflection magnitude between the presence and absence of heart muscle is 9.9%.

In one particular application, if a metallic object, such as a pacemaker lead 22L (shown in a dashed line in FIG. 1) were lodged inside the heart 22, or if a mechanical valve 22V (shown in a dashed line in FIG. 1) were used, then the reflection would be very high, such as 1.0 for a metal object, because metal is easily discerned from body tissue and has several times its reflection magnitude. Even if the metal object has a much smaller cross-section, as may be the case with the lead 22L, it is still easily discerned in practice as long as the polarization of the wire and the monitor antenna match—which is generally the case for the lead 22L, and for a vertical orientation of the monitor 1.

The present invention overcomes a serious limitation stemming from a variable reflection magnitude from the first surface of the chest wall 24. The problem of varying first surface reflection magnitude is caused by radiating a pulse that contains either post-shoot or ringing—a common effect when radiating pulses through an antenna. What radiates later in time falls into the sampler's gate when reflected off objects or tissue closer than the intended range gate 54, i.e. there is a displaced range gate. Accordingly, ringing components reflect off the front surface of the chest wall 24 and fold into the reflections from the heart 22 in simultaneity. Indeed, these front surface reflections can exceed the desired reflections.

The solution to this problem is accomplished by radiating a particular waveform with half-sine shape and no ringing.

Thus, in the preferred embodiment, the monitor 1 emits a pulse having the desired waveform. This can be accomplished by the proper design of the transmit antenna 18, where the dimensions are short relative to a ¼ wavelength as defined by the half-sine pulse.

If the waveform contains ringing or components deviating from a clean half-sine-shaped impulse, the response of the heart muscle moving through the range gate 54 would include multiple pulses, effectively multiplying the perceived heart rate. Accordingly, the transmit antenna 18 and the receive antenna 20 must not ring so both are resistively terminated and both are less than ¼ wavelength in dimension.

Figure 4:
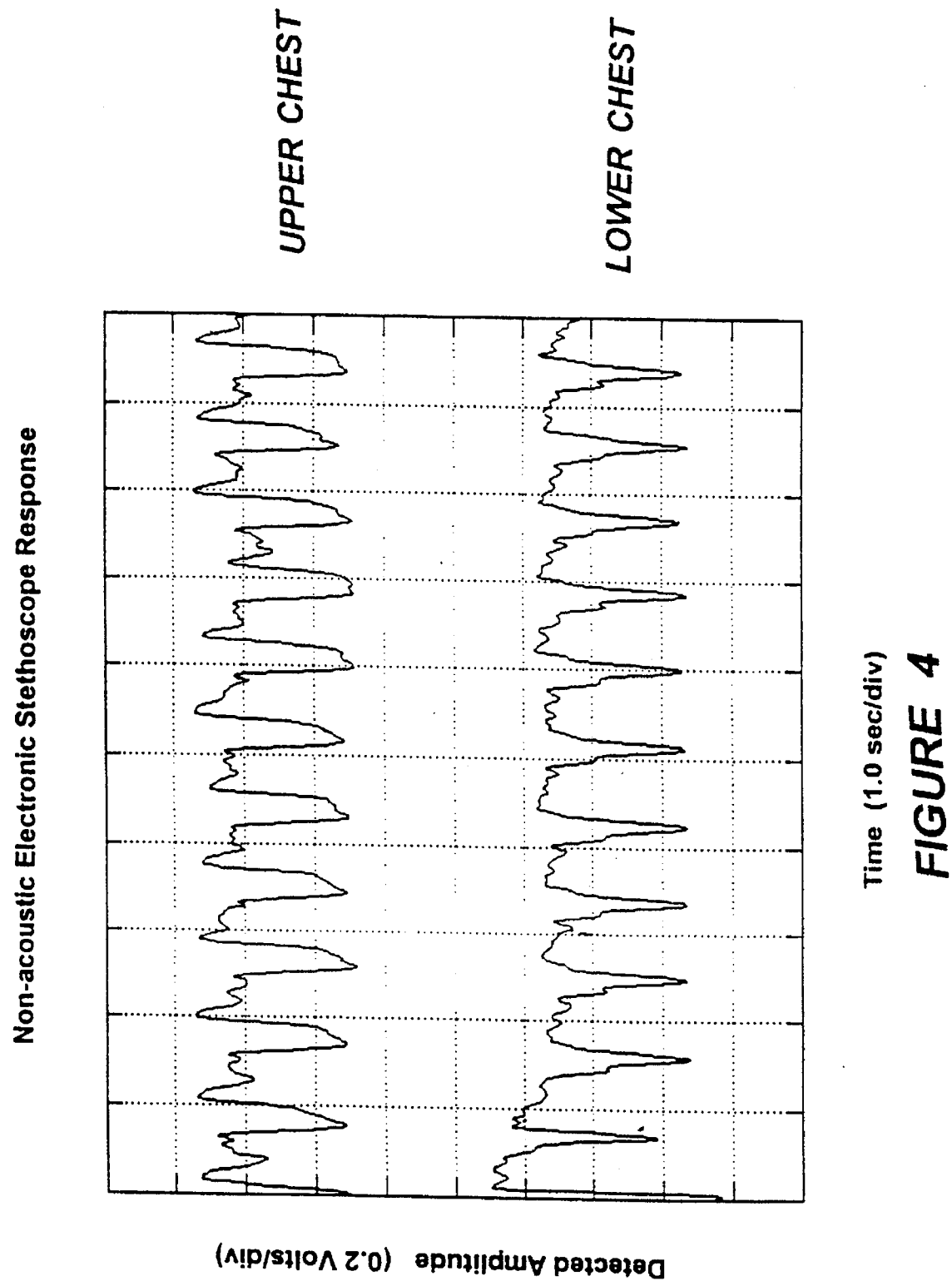
FIG. 4 illustrates two timing response charts plotting the signals received by the monitor of FIG. 1, at two positions in proximity to the heart.
Figure 5:
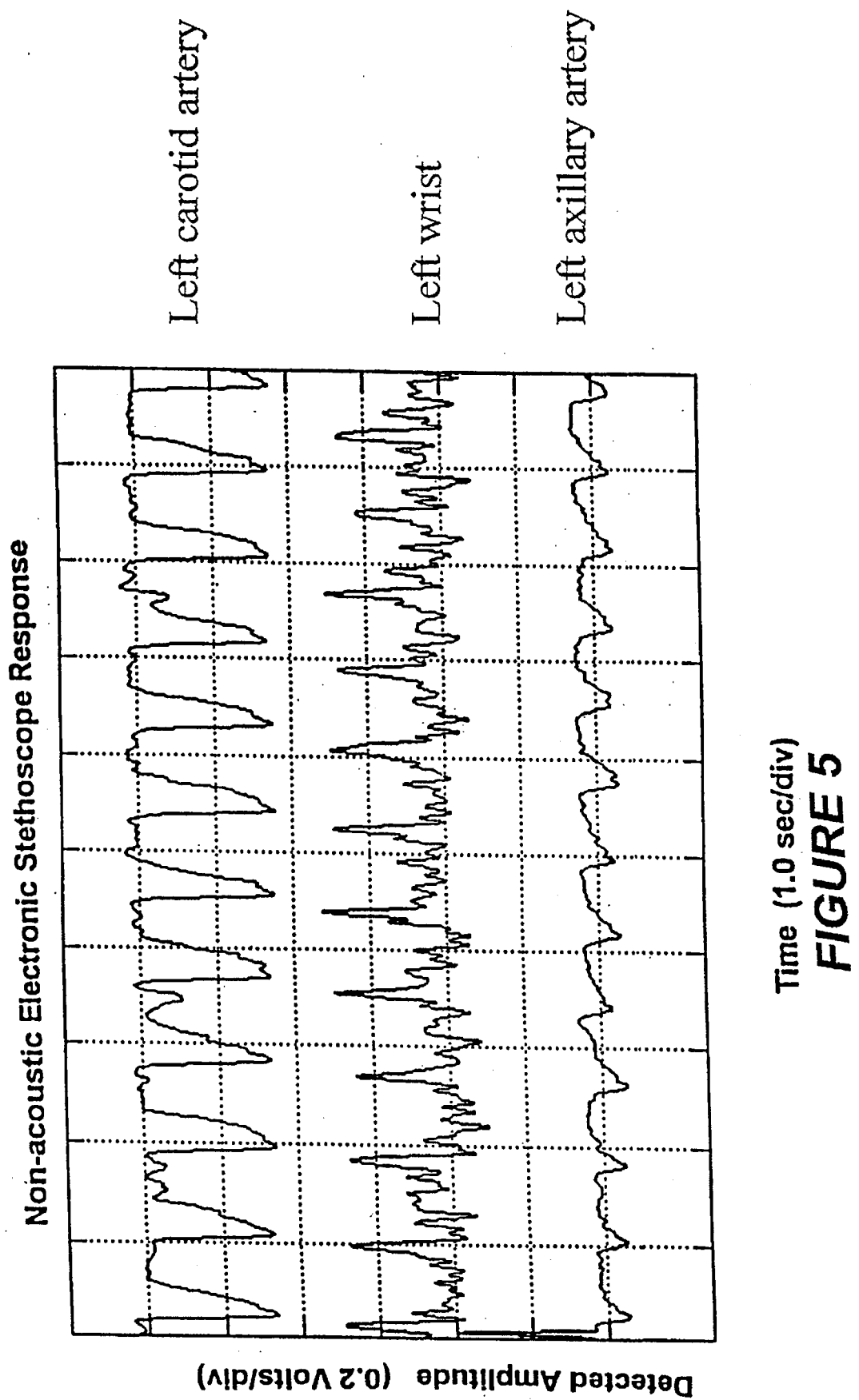
FIG. 5 illustrates four timing response charts plotting the signals received by the monitor of FIG. 1, and corresponding to signals reflected from various blood vessels.

FIG. 4 illustrates two timing response charts plotting the signals received by the monitor 1 of FIG. 1, at two positions in proximity to the heart. FIG. 5 illustrates three timing response charts plotting the signals received by the monitor 1, and corresponding to signals reflected from the left carotid artery, the left wrist, and the left axillary artery.

The timing of the range gate can be alternated between two range gates 54 and 54A (partially shown in a dashed line in FIG. 1). The corresponding detection voltage can be stored on two separate S/H circuits, as illustrated in the above referenced patent application entitled "Ultra-Wideband Radar Motion Sensor".

The operation of the second range gate 54A is similar to that of the first range gate 54, and each range gate 54, 54A can be independently controlled and set. As a result, the reflectivity from the independent range gates 54 and 54A can be processed independently or in conjunction with each other. For instance, if the first range gate 54 were set to detect the front wall 22F of the heart 22, and the second range gate 54A were set to detect the rear wall 22R of the heart 22, then significant and valuable information can be collected relating to the contraction and expansion cycle and condition of the heart 22.

The use of dual range gates 54 and 54A results in a "stereo" effect which perceptively places the listener between the front and rear walls of the heart 22. It should be understood that additional range gates can be used according to the same inventive principle described above.

Figure 6:
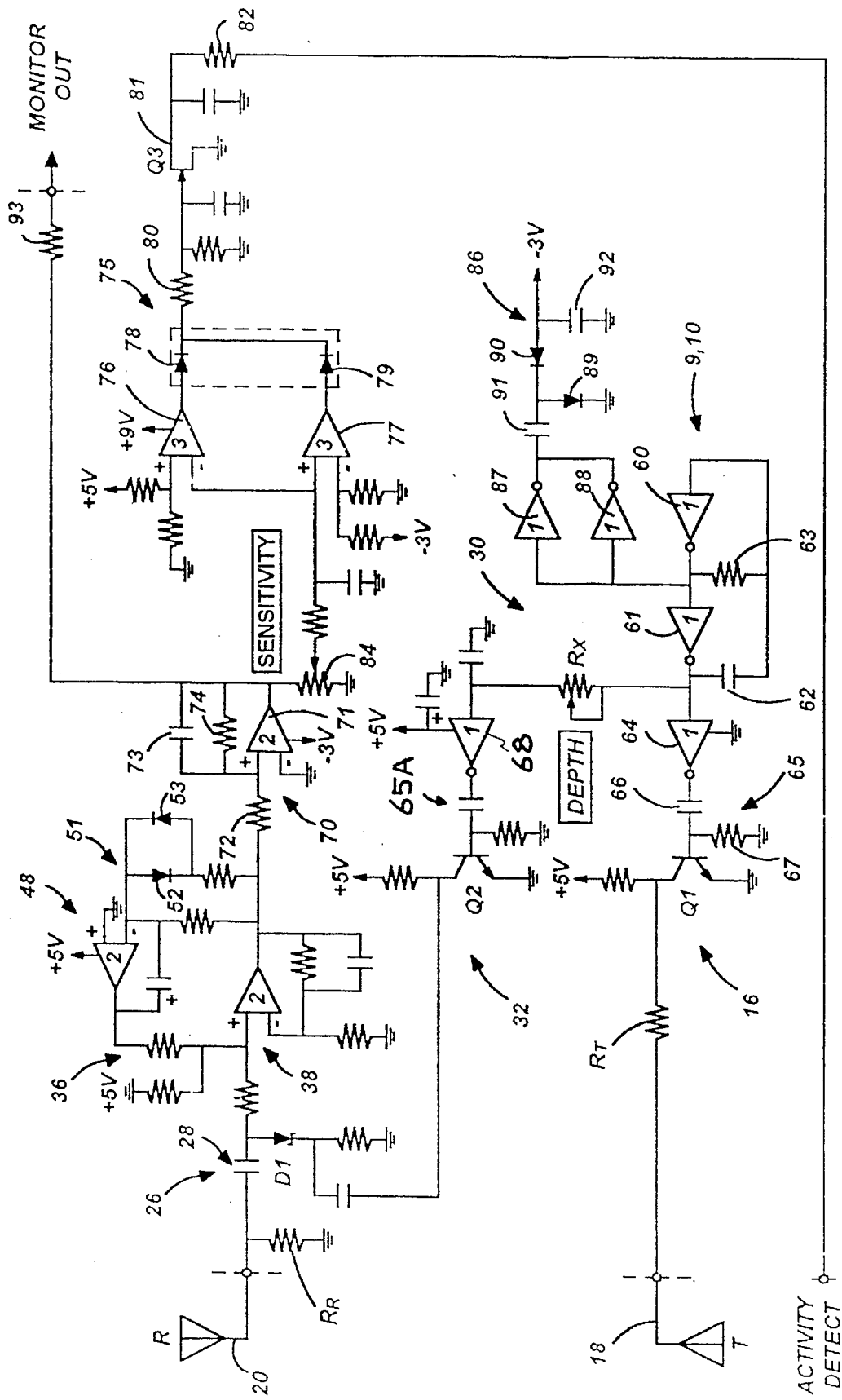
FIG. 6 is an exemplary circuit diagram of the monitor of FIG. 1.

FIG. 6 shows a prototype embodiment of the monitor 1. The 2 MHz PRF/PRI generator 10 and the noise generator 9 are collectively formed of two inverters (I1) 60, 61 connected in series; a capacitor 62 is connected between the output of the inverter 61 and the input of the inverter 60; and a shunt resistor 63 connected between the output and input of the inverter 60. The PRF/PRI generator 10 is followed by a buffer comprising an inverter (I1) 64, and a pulse width limiter 65 comprised of a capacitor 66 and a shunt resistor 67. The pulses pass to the impulse generator 16 formed of a transistor Q1=BFW92, whose collector is connected to the transmit antenna 18 through resistance $R_T$. The pulses from the PRF/PRI generator 10 also follow a second path through the range delay generator 30, which is formed of a variable resistance $R_x$, a stray capacitance and input capacitance of a buffer gate (68). The delayed pulse is input through another pulse width limiter 65A into impulse generator 32, formed of another transistor Q2=BFW92, which produces the gating pulse.

The reflected signals are picked up by the receive antenna 20 and input into S/H circuit capacitor 28 which is gated by the gating pulse through a Schottky diode D1=MBD701. The output from the S/H circuit 26 is input into amplifier (I2) 38. The input 36 of the amplifier 38 serves as the summer for the S/H circuit 26 output. The output of amplifier 38 represents the measured bio-potential, and can be used, connected to, or processed by various equipment and/or instruments, such as the headphone 42 (FIG. 1). In a preferred embodiment, I1=74HC04, I2=TLC274. Further, the propagating pulse will easily radiate across an air gap or material (such as muscle, blood, etc.) of several inches.

The output of the amplifier 38 is connected to an amplification circuit 70 to provide additional gain to the amplifier 38. The amplification circuit 70 includes an operational amplifier 71, which is connected to the output of the amplifier 38 via a resistor 72, and which is shunted by a capacitor 73 and a resistor 74 connected in parallel.

The output of the amplifier 71 is connected to a threshold detector network 75, for detecting whether the monitor output level exceeds predetermined upper and lower threshold levels. The threshold detector network 75 generally comprises two comparators or operational amplifiers 76, 77 (I3=TLC274) whose outputs are combined, via two diodes 78, 79 and a resistor 80, to a switch 81 (Q3). In operation, if either one of the upper or lower threshold levels is exceeded, the corresponding operational amplifier 76 or 77 drives the switch 81 into a conductive state. The output of the switch 81 can then be used to drive an alarm or any other appropriate circuit. For instance, if the monitor were used in conjunction with, or as part of a pacemaker, the output of the switch 81 is sensed, via an appropriate resistor 82 to provide a desired indication, such as activity detect, in order to initiate or inhibit pacing. The sensitivity of the threshold detector network 75 can be regulated by a potentiometer 84 so as to control the amplitude of the signal applied to the operational amplifiers 76, 77.

Figure 11:
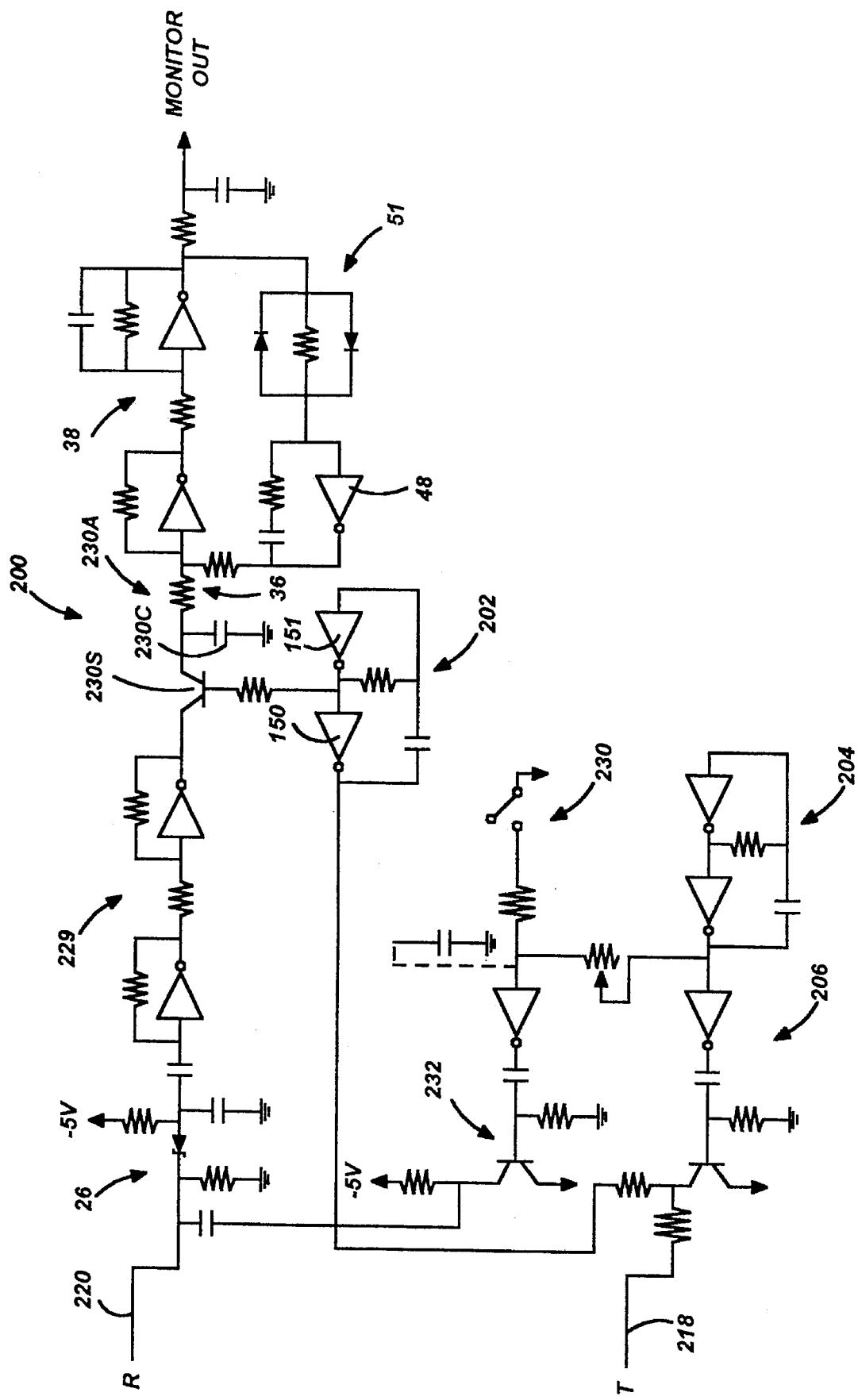
FIG. 11 is an exemplary circuit diagram of the monitor of FIG. 10.

A voltage rectifier network 86 is connected to the PRF/PRI generator 10 to supply −3 volts to various components of the monitor, such as the amplifier 71. The voltage rectifier network 86 generally includes two parallel inverters (I1) 87, 88 for supplying a 0–5 V square wave voltage. Two diodes 89, 90 are connected to the output of the inverters 87, 88, via a capacitor 91. A shunt capacitor 92 is connected to the diode 90, such that the voltage rectifier network 86 rectifies and level shifts the square wave voltage, in order to generate a −3 V steady output voltage. An output resistor 93 is connected to the output of the amplification circuit 70 to prevent excessive current drain. It should be noted that the values of many of the components shown in the circuit diagrams of FIGS. 6 and 11 are identified in the above U.S. patent applications Ser. Nos. 08/044,717 and 08/044,745, now U.S. Pat. Nos. 5,361,070 and 5,345,471.

Figure 7:
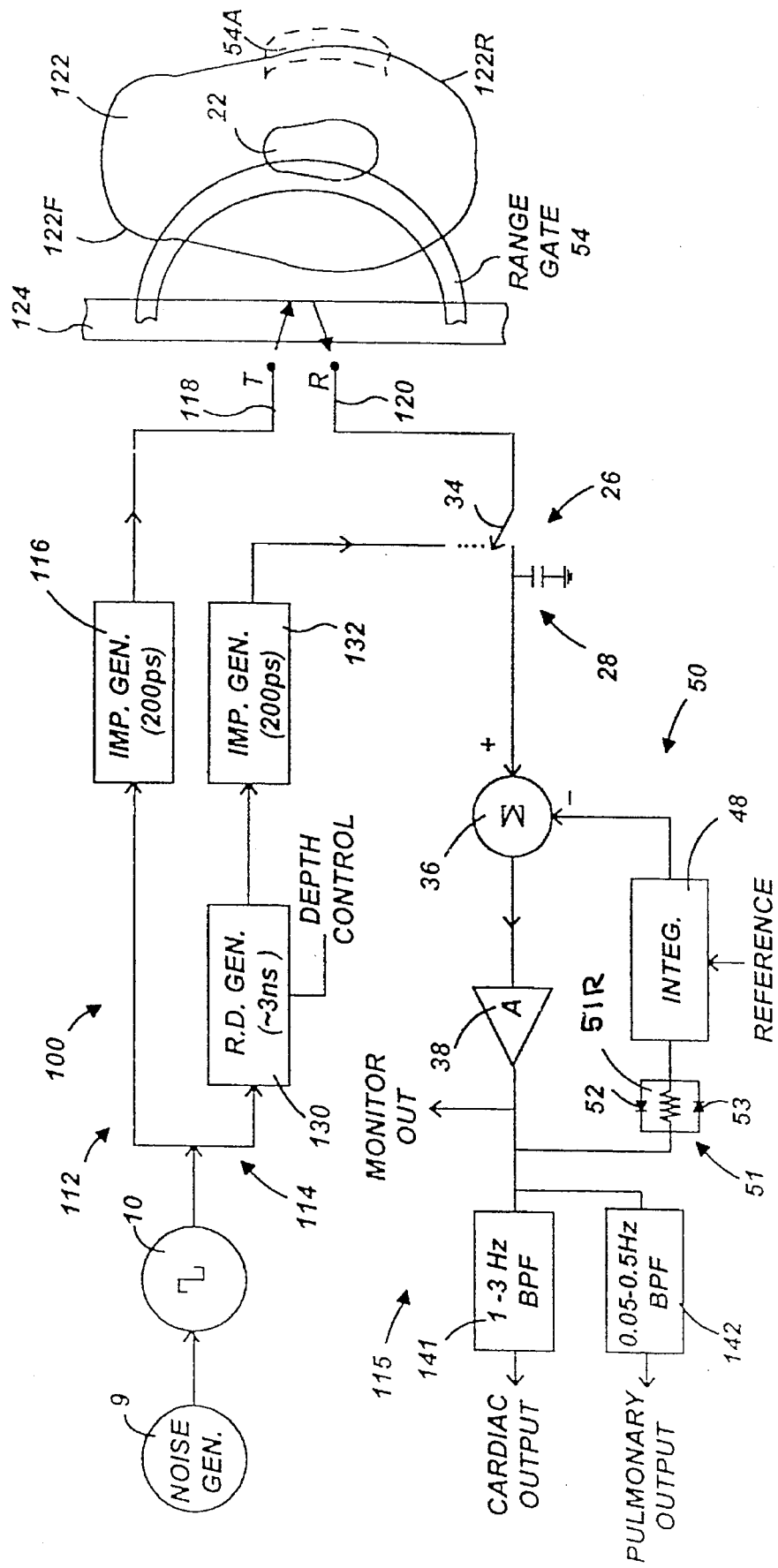
FIG. 7 is a block diagram of a non-contact cardiopulmonary monitor according to the present invention.

FIG. 7 illustrates another monitor 100, which operates in a generally similar way to the monitor 1 of FIG. 1, but has been modified for remotely detecting heart and respiratory motion through materials such as a mattress pad, a chair back, etc. The antennas of the monitor 100 have been modified to permit greater scanning range. The audible output has been deleted; however, one skilled in the art can optionally add this feature. A range control is provided, and can be set to detect respiration at a distance of about 6 feet. Identical numeral references in FIGS. 1 and 7 refer to identical components having identical functions.

The general operation of the monitor 100 is also based on the emission of a pulse from a transmit antenna, waiting for a brief period of time, and then opening a gate connected to a receive antenna to allow the reflected pulse to be sampled. However, in the particular application where the monitor is used as a non-contact cardiopulmonary monitor, the waiting period corresponds to 12 inches or more of round trip time of flight at the speed of light in free space (or in a combination of free space and one inch of tissue).

In the transmit path 112, the PRF/PRI generator 10 drives an impulse generator 116, which provides a 5 V 200 ps wide half-sine transmit pulse that is applied to a transmit antenna (T) 118. The electrical length of the transmit antenna 118 is set to be short relative to the spectral content of the half-sine to avoid ringing.

A receive antenna (R) 120 picks up the pulse reflected from a body organ, such as a lung 122 (with front and rear walls 122F and 122R, respectively) and a heart 22 behind a chest wall, or object such as a chair 124, and applies it to a sample/hold (S/H) circuit 26 that is gated by a gating pulse from a gating path 114. The gating pulse is delayed by approximately 3 nanoseconds from the time that the transmit antenna 118 radiates the pulse. Therefore, reflections occurring at about 12 inches from the antennas 118 and 120 are thereby sampled. Pulses from the PRF/PRI generator 10 which are input into the transmit path 112 are simultaneously input into the gating path 114 where they pass through a range delay generator 130 followed by an impulse generator 132, which produces a 200 ps wide gating pulse for controlling a gating switch 34. The timing relationships illustrated in FIG. 2 also apply to the monitor 100.

In the receive path 115, the output of the summation element 36 is amplified by the amplifier 38, typically 70 dB across a passband of 0.05–10 Hz, and applied, optionally, to cardiac and pulmonary bandpass filters 141 and 142, respectively.

Figure 8:
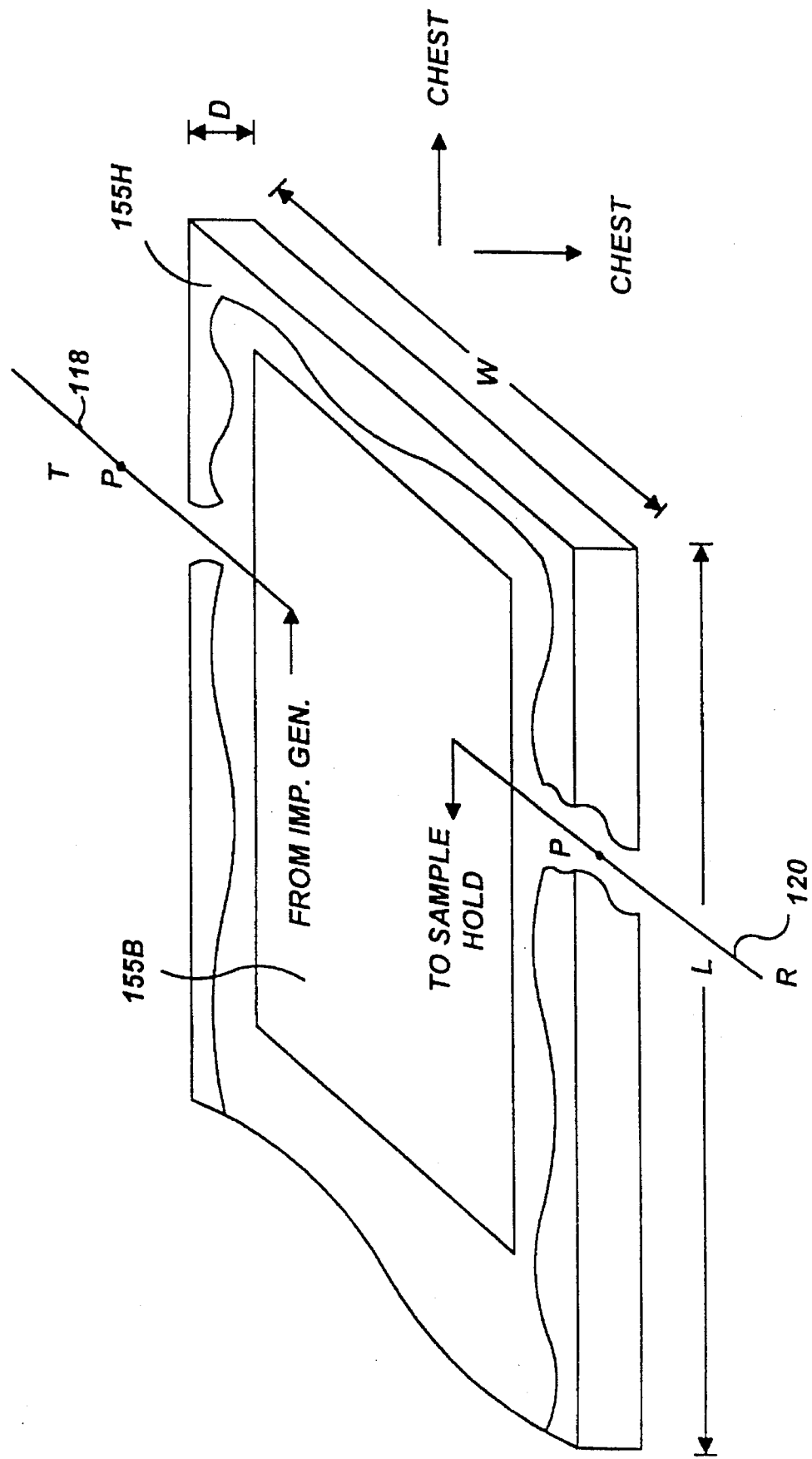
FIG. 8 is a schematic representation of an antenna forming part of the monitor of FIG. 7, and showing a cut-away view of a generally flat housing.

FIG. 8 is a schematic representation of an antenna 118, 120, forming part of the monitor 100 of FIG. 7, and showing a cut-away view of a generally flat and thin housing 155H. The antenna 118, 120 is a straight dipole, which alternatively can be folded, having a transmit element 118 and a receive element 120, each of which is about 0.5 in×2 in, but could be longer. The antenna can radiate electromagnetic waves within the 2 GHz band in compliance with FCC requirements.

The antenna by itself is self sufficient and does not need to be coupled to a ground plane 155B. The ground plane 155B holds the monitor circuitry. The antenna elements 118 and 120 can be telescopically extended or retracted for ease of storage, transport, and also for changing the effective length of the antenna elements. The antenna elements 118, 120 can be marked with various markings along their lengths, such as the marking points P, for various applications. For instance, the marking point P is placed at about half the full extended length of the antenna elements 118, 120 for pediatric use.

If the waveform contains ringing or components which deviate from a clean half-sine shaped impulse, the response of the heart muscle or lung boundary moving through the range gate 54 would include multiple pulses, effectively multiplying the perceived heart rate. Accordingly, the transmit antenna element 118 and the receive antenna element 120 are made to be non-ringing by resistively terminating them with resistors $R_T$ and $R_R$, respectively, as illustrated in FIG. 6. Consequently, the net T–R response is a clean half sine-shaped impulse.

The exact or optimal range gate 54 and/or 54A, can be determined by the following equations:

Range Gate=½[Flight time (Air)+Flight time (Tissue)].

$$\text{RangeGate} = \left[ \frac{\text{DistanceAir}}{C} + \frac{\text{DistanceTissue}}{C} \cdot \sqrt{\epsilon_r} \right],$$

where C is the speed of light, and $\epsilon_r$ is the dielectric constant of the tissue. The timing of the range gate 54 can be swept over a set of ranges to broaden the effective response range. Otherwise, with a fixed range gate optimized for 12 inches, cardiopulmonary detection holds from 0 to 12 inches, and pulmonary detection holds from 0 to 18 inches. The cardiac bandpass filter 141 and the pulmonary bandpass filter 142 (FIG. 7) selectively filter the signal at the output of the amplifier 38 in order to separate and identify the pulmonary motion from the heart motion. Typically, the cardiac rate ranges between 40 beats or less per minute to 180 beats per minute, while the breathing rate ranges between 2 or more to 20 breaths per minute. It should however be understood that other ranges can be selected depending on the desired applications. The circuit diagram of the monitor 100 is basically similar to the circuit diagram of the monitor 1, illustrated in FIG. 6, such that the monitor output, at the output of the amplifier 38 is connected to the two bandpass filters 141 and 142.

Figure 9:
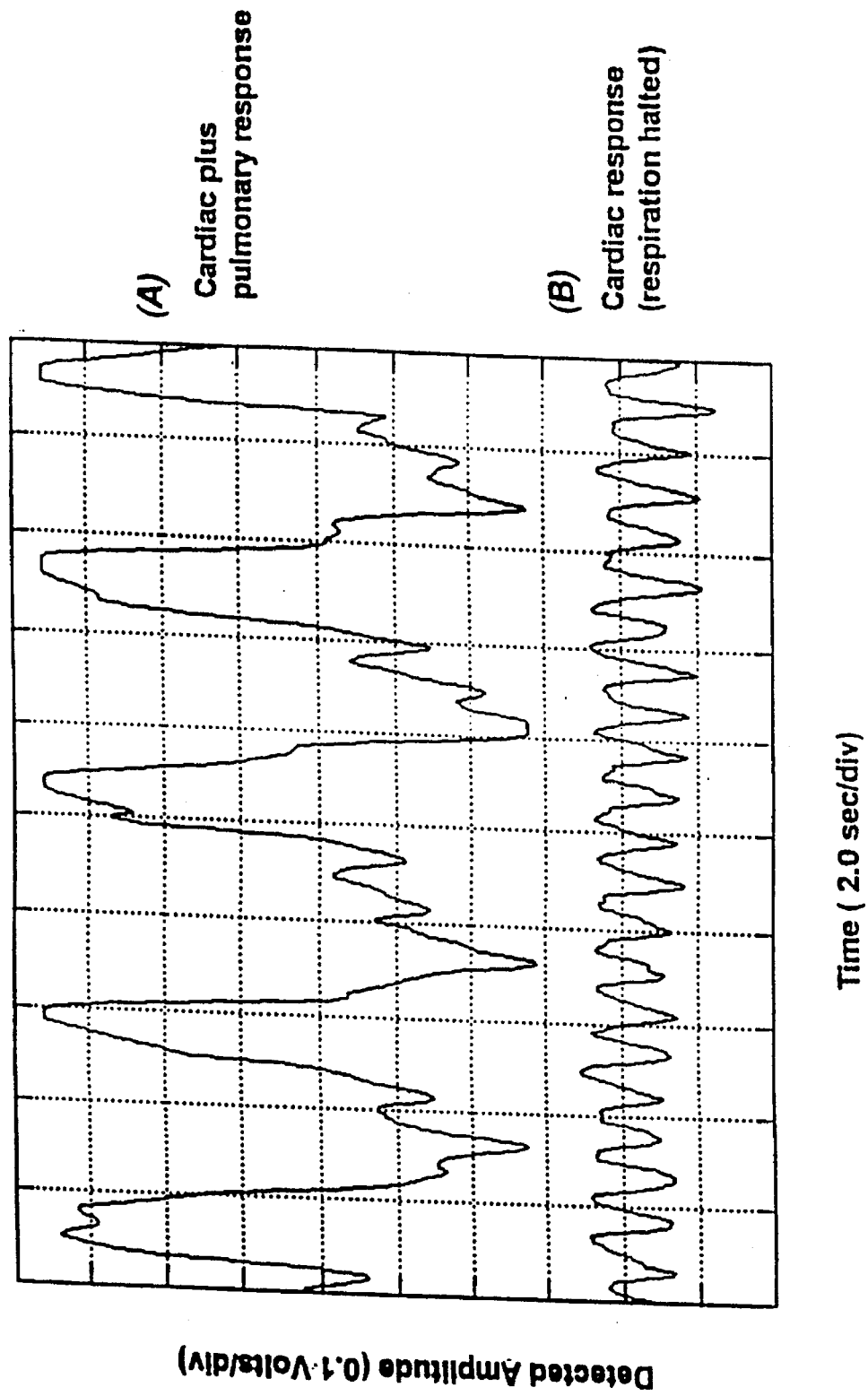
FIG. 9 illustrates two timing response charts plotting the signals received by the monitor of FIG. 7, such that the upper chart represents cardiac and pulmonary response, and the lower chart represents the cardiac response with the respiration halted.

FIG. 9 illustrates two timing response charts (A) and (B) plotting the signals received by the monitor 100. The upper chart (A) represents a combined cardiac and pulmonary response, and the lower chart (B) represents the cardiac response with the respiration halted. The data for both charts were obtained with the chest wall 124 positioned at a range of about 12 inches from the monitor 100. The data is the voltage or bio-potential at the output of the amplifier 38.

Figure 10:
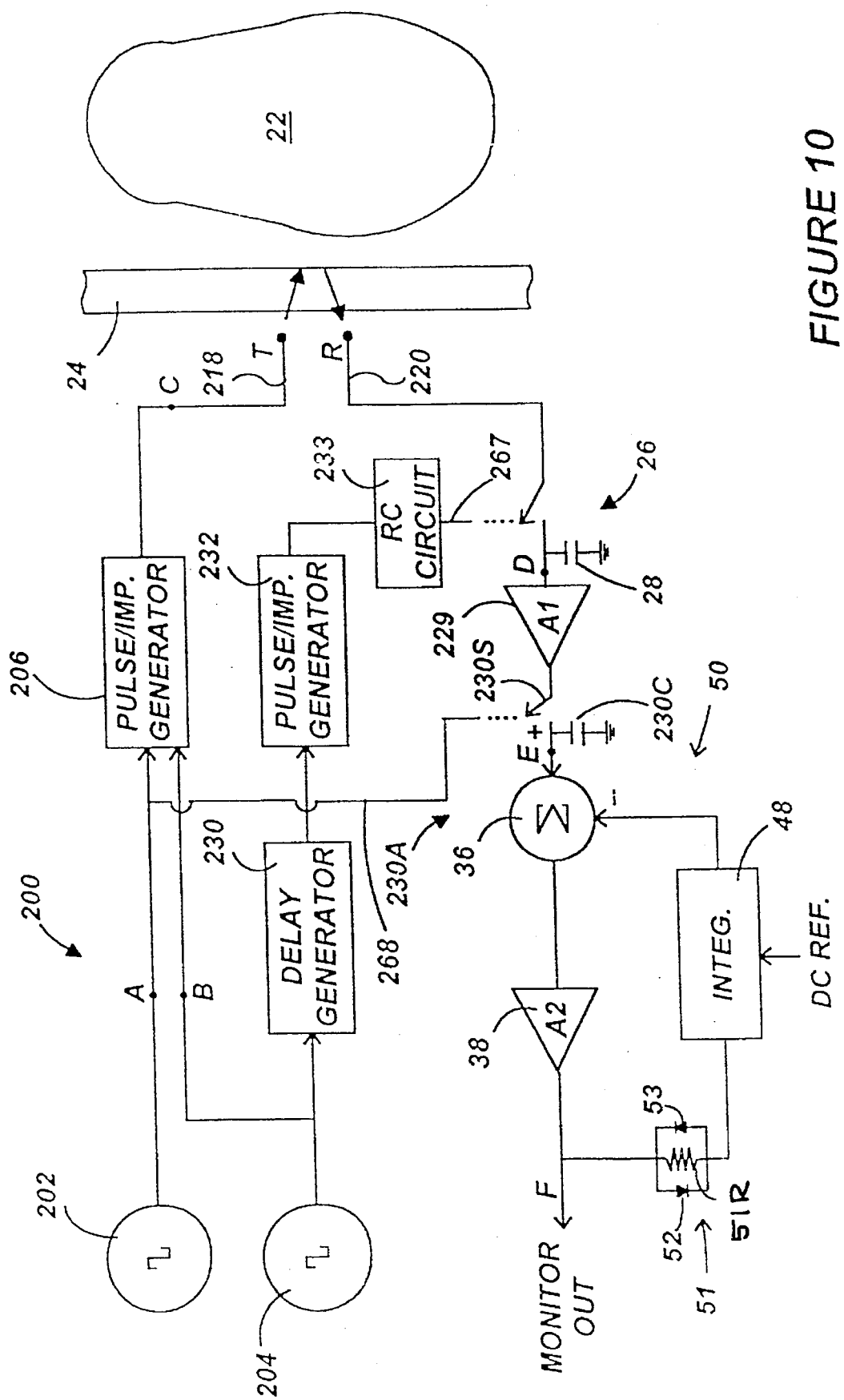
FIG. 10 is a block diagram of yet another embodiment of a monitor according to the present invention using a homodyne circuit.

FIG. 10 is a block diagram of yet another embodiment of a monitor 200 using a homodyne circuit. The homodyne circuit is described in the PCT patent application entitled "Electromagnetic Hidden Object Detector", serial number PCT/US/94-04813, filed on May 9, 1994, by Thomas E. McEwan, which is incorporated herein by reference.

The monitor 200 generally includes an AC coupled amplifier in the receiver path that prevents DC signals from passing from the averaging sample and hold circuit to the monitor output. This AC coupled amplifier filters out the DC bias level shifts in the S/H circuit 26. An AC modulation is impressed upon the transmitter pulses, and this AC modulation is then synchronously rectified in the receiver (homodyne technique), thereby permitting the use of the AC coupled amplifier in the receiver.

In summary, the monitors 1 and 100 have been modified for homodyne operation. The homodyne technique involves modulating a signal from a PRF generator prior to radiation and detection with a continuous wave (CW) signal. The receive amplifier then operates with a passband centered on the CW signal and is thus AC coupled. After amplification, the signal is synchronously detected using the same CW signal.

The monitor 200 includes a homodyne oscillator 202 which typically operates at several kHz (in the present example 2 kHz), and a PRF generator 204 (similar to the PRF generator 10 shown in FIG. 1), which generally operates in the range of 1 MHz to several MHz (i.e., 2 MHz in the particular example described hereafter). It should be clear that the homodyne signal can alternatively be an arbitrary sequence of pulses having a mean frequency on the order of several kHz and a zero average.

The signals from the homodyne oscillator 202 and the PRF generator 204 are fed into a step or impulse generator 206 where the homodyne oscillator 202 amplitude modulates the step signal generated by the impulse generator 206, in effect turning the impulse generator ON and OFF at the desired homodyne frequency, which in this example is 2 kHz. Therefore, the signal output by the impulse generator 206 and transmitted by the transmit antenna 218, includes periodic packets of pulses having a frequency of 2 kHz, such that each pulse typically comprises bursts (such as 1,000 pulses) at a frequency of 2 MHz, with a 0.5 millisecond burst interval.

As the pulses are transmitted over the transmit antenna 218, they are reflected off the walls of a moving object, which in the present example is a heart (or lung) 22 for reception by the receive antenna 220. The signals reflected off the heart 22 are formed of a sequence of periodic pulses, corresponding to the transmitted packets, and having a frequency of 2 kHz. At the receive antenna 220, the amplitude of the 2 kHz envelope is related to the reflection from the heart 22.

In one embodiment of the present monitor 200, it is desired to reference the 2 kHz envelope to a predetermined reference level from the integrator 48, thus allowing the monitor 200 to basically operate similarly to the monitors 1, 100. For this purpose, a receiver sample and hold circuit 26 averages the 2 MHz bursts (pulses) over a period of about 0.1 millisecond, so that only the 2 kHz homodyne frequency remains on the sample and hold capacitor 28. The homodyne frequency is amplified by an AC coupled amplifier 229, and is thereafter synchronously rectified into a DC level by means of a synchronous rectifier 230A.

The synchronous rectifier 230A includes a capacitor 230C and a rectifier switch 230S. The rectifier switch 230S includes a saturated transistor, and the capacitor 230C, is typically on the order of 0.01 microfarad and is used to hold the value of voltage at the output side of rectifier switch or transistor 230S, when the latter is driven into conduction by the homodyne oscillator 202.

The advantage of the AC amplifier 229 is that the monitor DC bias levels, i.e., the DC bias levels at the sample and hold circuit 26 are not allowed to pass through (i.e., filtered out). These DC bias levels vary with the power supply fluctuations and with materials brought into near proximity to the receive antenna 220. The rectified DC level at the output of the synchronous rectifier 230A represents the reflected pulses from the heart 22, and the subsequent operation of the monitor 200 is similar to that of the monitors 1 and 100.

In operation, the rectifier switch 230S closes during one half of the homodyne oscillator cycle, and charges the capacitor 230C during this half cycle. During the complementary (i.e., remaining) half cycle of the homodyne oscillator cycle the switch 230S is open, and the rectifier 230A does not detect the signals from the homodyne oscillator 202. As a result, the average signal applied to the capacitor 230C represents the peak amplitude of the signal (square wave) at the output of the AC coupled amplifier 229, thereby generating a DC voltage which corresponds to the reflection signal from the heart 22 and not from the DC voltage from the sample and hold circuit 26.

The DC voltage developed on the capacitor 230C represents the summation of the desired signals reflected from the heart 22, as well as undesirable reflections from various sources including the monitor housing and direct antenna-to-antenna coupling. The output of the DC coupled amplifier 38 is caused to be equal to DC Reference voltage.

FIG. 11 is an exemplary circuit diagram of the monitor 200 of FIG. 10. The monitor includes a homodyne oscillator 202, which typically comprises two CMOS inverters 150, 151. The outputs of the homodyne oscillator 202 are connected to the impulse generator 206 and the synchronous rectifier 230A.

The receive path of the circuit of the monitor 200 is generally similar to that of the monitors 1 and 100; and includes the AC coupled amplifier 229 and the synchronous rectifier 230A. The AC coupled amplifier 229 is connected between the averaging sample and hold circuit 26 and the synchronous rectifier 230A which is connected to the summer 36. The AC coupled amplifier 229 includes two MC14069UB CMOS inverters by Motorola, used in a linear mode as amplifiers. The synchronous rectifier 230A includes a bipolar transistor, e.g. 2N2222 by National Semiconductor, that is turned ON or OFF by the homodyne oscillator 202.

The DC coupled amplifier 38 includes two MC 14069UB inverters by Motorola used in the linear mode as amplifiers. Similarly, the integrator 48 includes an MC14069UB inverter. The output of the DC amplifier is processed as desired. While the circuits of the disclosed embodiments have been described in term of discrete components for simplicity and clarity purpose, these circuits can alternatively be miniaturized by integrating these components on an integrated circuit or chip.

Figure 12:
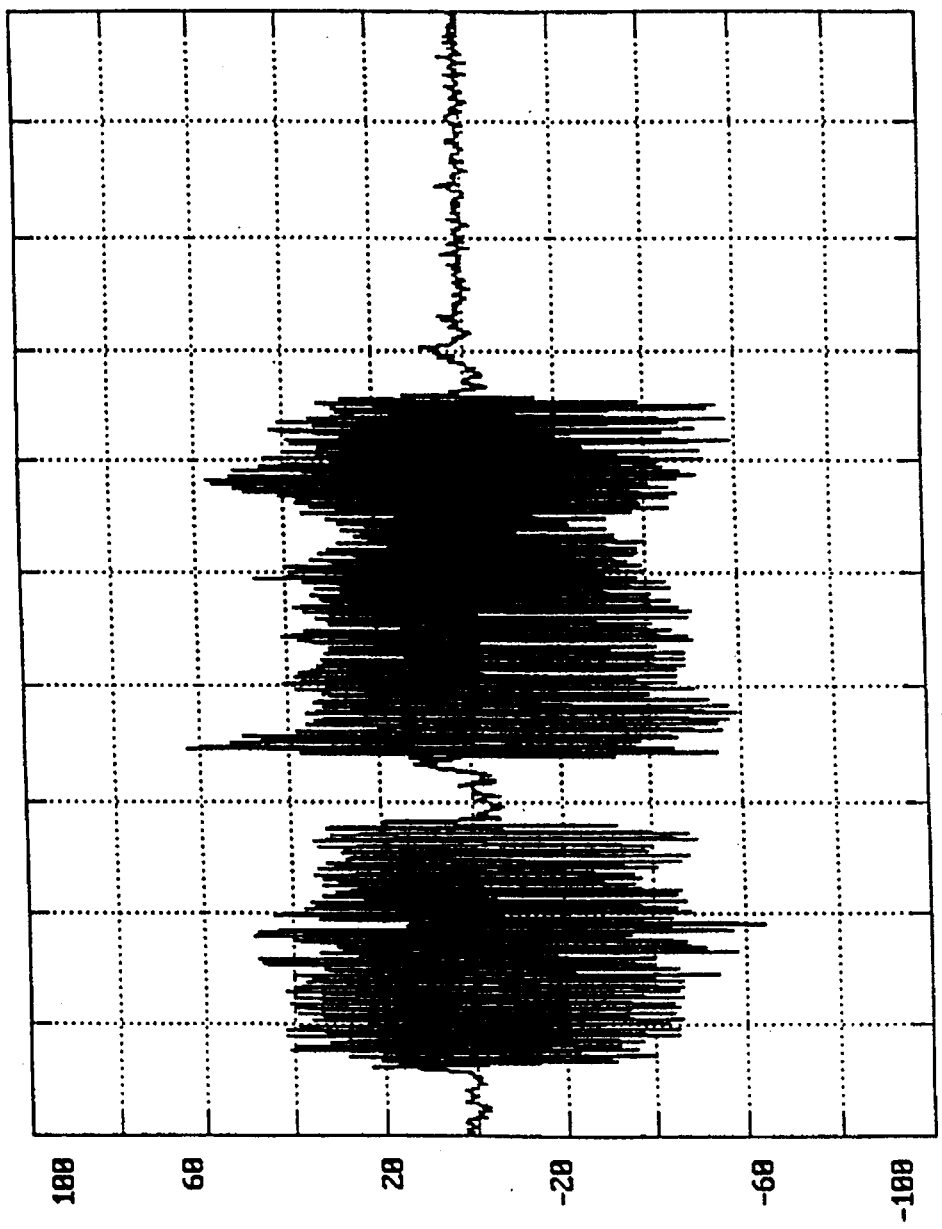
FIG. 12 is a timing graph using the inventive monitor of FIG. 1 as a throat microphone, corresponding to, and illustrating the spoken words "one thousand".

The monitors 1, 100 and 200 can also be used as microphones in several applications. For example, FIG. 12 is a timing graph which illustrates the use of the inventive monitor 1 as a throat microphone, and which corresponds to, and graphically displays the spoken words "one thousand". It should be understood that the monitors 100 and 200 can also be adapted for use as throat microphones. In operation, the throat microphone is positioned over the region of the Adam's apple or in close proximity thereto in order to monitor and measure the movement of the vocal chords. In one design of the throat microphone, the amplifier 38 of FIG. 1 has a bandwidth range of 20 Hz to 3 KHz, and the monitor output can be used without a voltage controlled oscillator in order to provide audible sounds.

Another exemplary application of the throat microphone is the identification of lesions or other abnormalities in the vocal chords region, by acoustically exciting such region. An acoustic excitation is applied from the mouth toward the throat and the present throat microphone is used to record the resulting response. A lesion or abnormality would produce an abnormal resonance which would be detected and measured by the throat microphone. Similarly, the ear drums can be excited and the corresponding vibration response detected by the microphone and recorded for various diagnostic purposes.

The present monitor/microphone can alternatively be used in conjunction with mechanical or acoustic stimulation sources. For instance, if an acoustic beam is focused on an tumorous area, the tumor could resonate at a predetermined frequency characteristic of its particular nature. The monitor/microphone can detect the resonance movement and help identify the tumor type and location. Additionally, the present monitor/microphone can be used to determine bone conduction. An acoustic or mechanical stimulation source is impressed at one end of the bone of interest, and the monitor/microphone is positioned at various sites along the length of the bone, for measuring and detecting the propagation of stimulus by the bone. Cracks or similar abnormalities could produce anomalous or irregular sounds or indications.

The inventive monitor/microphone can be used to listen to the internal sounds of the lungs, for detecting abnormal murmurs, or other movements characteristic of symptoms associated with particular diseases or illnesses. The monitor/microphone can also be used to identify a fracture in an implanted metallic heart valve or other similar objects. For example, the monitor/microphone is capable of identifying fractures in a mechanical heart valve by detecting changes in the radar reflectivity (i.e., radar cross section or RCS) of the valve as the defect or crack generates an intermittent electrical contact.

The foregoing description of the invention has been presented for purposes of illustration and description. It is not intended to be exhaustive or to limit the invention to the precise forms described, and many other modifications are possible in light of the above teaching.

Some exemplary applications include but are not limited to: (1) pacemakers, whereby the monitors and variations thereof are implanted to sense the heart wall movement, and are used as, or in conjunction with conventional pacemaking principles and technology; (2) telemetry; (3) fluoroscopy; (4) fetal monitor equipment; (5) detector of objects lodged inside the body; (6) sudden infant death syndrome (SID); (7) electrocardiography (EKG); (8) echocardiography; (9) imaging, measuring and scanning monitors and methods, whereby the monitors can be used as substitutes for, or in conjunction with conventional systems such as ultrasound devices, NMR, NMI, etc., for imaging various organs, members or tissues, including but not limited to the uterus, fetus, ovaries, bones, blood clots, brain, spinal chord, muscles, prostate, thyrohyoid membrane, etc.; (10) bone fracture screening monitors; (11) enhancement to mammography; (12) internal guiding or scanning devices to be inserted inside tubular or other structures such as blood vessels, the bronchial tree of the lungs, the gastrointestinal tract, the genital tract, or the urinary tract using an angioscope, endoscope or catheter.

What is claimed is:

1. A monitor for detecting the movement of one or more body parts, comprising;

(a) a pulse generator for producing and simultaneously inputting a sequence of pulses to a transmit path and a gating path;

(b) an impulse generator connected to said pulse generator for producing corresponding transmit pulses;

(c) a transmit antenna connected to impulse generator to transmit said transmit pulses toward the one or more body parts;

(d) a range delay generator connected to said pulse generator for generating timed gating pulses;

(e) a receive antenna;

(f) a sampling receiver connected to said receive antenna in a receive path;

(g) said range delay generator being connected to said sampling receiver and producing timed gating pulses at a fixed range corresponding to the location of the one or more body parts so that said timed gating pulses cause said sampling receiver to selectively sample pulses reflected from the one or more body parts and received by said receive antenna to produce an averaged sampled signal;

(h) a signal processor connected to said sampling receiver for detecting changes in the averaged sampled signal and providing an output signal indicative of motion of said one or more body parts.

2. The monitor according to claim 1, for detecting movement of a heart;

wherein said signal processor includes means for producing non-acoustic indications of the movement of the heart.

3. The monitor according to claim 2, for detecting movement of a lung;

wherein said signal processor includes means for producing non-acoustic indications of the movement of the lung.

4. The monitor according to claim 2, for detecting movement of both a heart and a lung;

wherein the output signal corresponds to the physical movement of the heart and lung; and wherein said signal processor includes means for separating the output signal into a cardiac output indicative of the physical movement of the heart, and a pulmonary output indicative of the physical movement of the lung.

5. The monitor according to claim 4, wherein the separating means comprises a bandpass filter for separating said output signal into said cardiac output.

6. The monitor according to claim 4, wherein the separating means comprises a bandpass filter for separating said output signal into said pulmonary output.

7. The monitor according to claim 1, wherein said sampling receiver comprises a sample and hold circuit that is gated by said gating pulses from said gating path.

8. The monitor according to claim 7, wherein said range delay generator produces a gating pulse which is delayed by approximately 2 nanoseconds (2 ns) from the time that said transmit antenna radiates a transmit pulse; and further comprising an impulse generator connected between the range delay generator and the sample and hold circuit which produces a 200 ps gating pulse for gating said sample and hold circuit.

9. The monitor according to claim 1, wherein said range delay generator comprises an adjustable fixed delay so that the timed gating pulses determine the range gating of the monitor to the one or more body parts.

10. The monitor according to claim 9, wherein said sampling receiver comprises a sample and hold circuit that is gated by said gating pulses from said gating path; and wherein said sample and hold circuit samples the pulses along said receive path at least 1,000 times and produces an averaged sample signal with a peak value substantially equal to that of a reflected pulse.

11. The monitor according to claim 9, wherein said signal processor further includes a summation element connected to the sample and hold circuit which subtracts background reflections, and an amplifier connected to the summation element for amplifying the output of said summation element.

12. The monitor according to claim 11, further comprising an audio oscillator which has its output multiplied by the output from said amplifier; and wherein the output of said audio oscillator is frequency modulated by the rate of change of the signal from said amplifier for generating a Doppler effect that is related to the velocity of the movement of said body parts.

13. The monitor according to claim 11 further comprising a differentiation circuit connected to said amplifier for deriving the rate of change of the signal from said amplifier.

14. The monitor according to claim 11, wherein said signal processor further includes a feedback path comprising an integrator which servo's the output of said amplifier until an equilibrium is reached, such that the output of said amplifier is forced to equal a reference voltage applied to said integrator.

15. The monitor according to claim 11, further including a dual time constant circuit such that for large signals related to gross sensor motion relative to pulmonary motion, there is a fast AC coupling time constant, and for normal signal levels related to heart motion there is a much slower AC coupling time constant.

16. The monitor according to claim 15, wherein said dual time constant circuit includes two oppositely oriented diodes shunted by a resistor.

17. The monitor according to claim 1, wherein said range delay generator produces alternating delays so that the timed gating pulses determine at least a first and second range gates.

18. The monitor according to claim 1, further comprising a homodyne oscillator connected to the impulse generator which generates homodyne signals to modulate the transmit pulses, and a demodulator connected to the sampling receiver and the homodyne oscillator to remove said modulation from the sampled reflected pulses.

19. The monitor according to claim 18, wherein said homodyne signals are fed to said impulse generator for selectively switching ON and OFF said impulse generator at a predetermined homodyne frequency.

20. The monitor according to claim 18 wherein said demodulator comprises a synchronous rectifier.

21. The monitor according to claim 1 for detecting movement of the vocal chords wherein the signal processor includes means for passing output signals in a bandwidth range of about 20 Hz–3 KHz.

22. Method for monitoring the movement of one or more internal body parts, comprising:

(a) simultaneously inputting a sequence of pulses to a transmit path and a gating path;

(b) producing transmit pulses in said transmit path from said input sequence of pulse and launching said transmit pulses toward the one or more internal body parts;

(c) generating timed gating pulses in said gating path from said input sequence of pulses, said gating pulses defining a fixed range gate at the position of the one or more body parts;

(d) selectively receiving pulses reflected from the one or more body parts by receiving reflected signals coincident with the timed gating pulses;

(e) sampling and storing said selected reflected pulses to produce an averaged sampled signal;

(f) detecting changes in the averaged sampled signal to detect movement of the one or more body parts.

23. The method of claim 22 further comprising directing said transmit pulses towards any of the heart, lungs, and vocal chords; selecting said fixed range gate to receive signals reflected therefrom; and producing an output signal indicative of movement thereof.

* * * * *